(12) United States Patent
Nomura et al.

(10) Patent No.: US 9,085,537 B2
(45) Date of Patent: Jul. 21, 2015

(54) PHOTOELECTRIC ELEMENT AND IMAGING DEVICE AND DRIVING METHODS THEREFOR

(75) Inventors: Kimiatsu Nomura, Kanagawa (JP); Tetsuro Mitsui, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 553 days.

(21) Appl. No.: 13/574,969

(22) PCT Filed: Feb. 8, 2011

(86) PCT No.: PCT/JP2011/053063
§ 371 (c)(1),
(2), (4) Date: Jul. 24, 2012

(87) PCT Pub. No.: WO2011/099606
PCT Pub. Date: Aug. 18, 2011

(65) Prior Publication Data
US 2012/0298846 A1     Nov. 29, 2012

(30) Foreign Application Priority Data

Feb. 9, 2010   (JP) ................................. 2010-026993
Jan. 27, 2011   (JP) ................................. 2011-015843

(51) Int. Cl.
| | | |
|---|---|---|
| H01L 51/42 | (2006.01) | |
| C07D 223/26 | (2006.01) | |
| C07D 209/86 | (2006.01) | |
| C07D 209/88 | (2006.01) | |
| C07D 219/14 | (2006.01) | |
| H01L 27/146 | (2006.01) | |

(52) U.S. Cl.
CPC ............ *C07D 223/26* (2013.01); *C07D 209/86* (2013.01); *C07D 209/88* (2013.01); *C07D 219/14* (2013.01); *H01L 27/14623* (2013.01); *H01L 27/14621* (2013.01); *H01L 27/14645* (2013.01)

(58) Field of Classification Search
CPC ................... H01L 27/14623; H01L 27/14645; H01L 51/42; H01L 27/14
See application file for complete search history.

(56) References Cited

U.S. PATENT DOCUMENTS

| | | | |
|---|---|---|---|
| 5,536,588 A | 7/1996 | Naito | |
| 5,550,290 A | 8/1996 | Mizuta et al. | |
| 7,619,254 B2 * | 11/2009 | Lee et al. | 257/72 |

(Continued)

FOREIGN PATENT DOCUMENTS

| | | |
|---|---|---|
| JP | 6-122277 A | 5/1994 |
| JP | 6-338392 A | 12/1994 |

(Continued)

OTHER PUBLICATIONS

Communication dated Mar. 29, 2011 issued by the Japanese Patent Office in corresponding Japanese Application No. 2011-015843.

(Continued)

*Primary Examiner* — Tony Ko
(74) *Attorney, Agent, or Firm* — Sughrue Mion, PLLC

(57) ABSTRACT

A photoelectric element includes a conductive layer, an organic photoelectric layer, a blocking layer and a transparent conductive layer, the organic photoelectric layer contains a p type organic photoelectric material having a glass transition temperature of 100° C. or higher and forms an amorphous layer, and the blocking layer contains a blocking material having a glass transition temperature of 140° C. or higher.

14 Claims, 2 Drawing Sheets

(56) References Cited

U.S. PATENT DOCUMENTS

| | | |
|---|---|---|
| 2005/0005964 A1 | 1/2005 | Komatsu |
| 2005/0098207 A1 | 5/2005 | Matsumoto et al. |
| 2006/0008740 A1 | 1/2006 | Kido et al. |
| 2006/0071253 A1 | 4/2006 | Nii |
| 2007/0034859 A1 | 2/2007 | Tierney et al. |
| 2008/0035965 A1 | 2/2008 | Hayashi et al. |
| 2009/0189058 A1 | 7/2009 | Mitsui et al. |
| 2009/0223566 A1 | 9/2009 | Mitsui et al. |

FOREIGN PATENT DOCUMENTS

| | | |
|---|---|---|
| JP | 7-324059 A | 12/1995 |
| JP | 2003-272861 A | 9/2003 |
| JP | 2005-32852 A | 2/2005 |
| JP | 2005-166637 A | 6/2005 |
| JP | 2006-24791 A | 1/2006 |
| JP | 2006-100508 A | 4/2006 |
| JP | 2006-521008 A | 9/2006 |
| JP | 2007-123707 A | 5/2007 |
| JP | 2008-72090 A | 3/2008 |
| JP | 2009-193774 A | 8/2009 |
| JP | 2009-200482 A | 9/2009 |

OTHER PUBLICATIONS

Written Opinion (PCT/ISA/237) of the International Searching Authority issued in corresponding International Application No. PCT/JP2011/053063 on May 24, 2011.

International Search Report (PCT/ISA/210) issued by the International Searching Authority in corresponding International Application No. PCT/JP2011/053063 on May 24, 2011.

\* cited by examiner

PHOTOELECTRIC ELEMENT AND IMAGING DEVICE AND DRIVING METHODS THEREFOR

TECHNICAL FIELD

This invention relates to a photoelectric element, an imaging device, and a method for driving the element and the device.

BACKGROUND ART

A flat light sensor is widely used as a solid-state imaging device, in which photoelectric conversion units (pixels) are two-dimensionally arrayed in a semiconductor, and a signal charge generated by photoelectric conversion in each pixel is transferred and read out by a CCD or a CMOS circuit. Conventional photoelectric units generally have a semiconductor substrate such as a silicon substrate having formed therein a pn junction to provide a photodiode.

With the recent trend to increase the number of pixels, the pixel size has been made smaller, and the area of the individual photodiodes is getting smaller accordingly. This of necessity raises the problem of reduction in the effective area of the photodiode, i.e., reduction of a pixel aperture ratio and reduction in light collection efficiency, resulting in reduction of sensitivity. As a means for improving the aperture ratio and so on a solid state imaging device having an organic photoelectric layer made of an organic material has been under study.

Incorporating a bulk heterojunction structure containing a fullerene or a fullerene derivative to an organic photoelectric layer is known effective to obtain high photoelectric conversion efficiency (high exciton dissociation efficiency). For example, JP 2007-123707A discloses a photoelectric layer containing a fullerene or its derivative.

While the organic photoelectric element used in a solar cell, which is designed to generate electric power, does not need application of an external electric field, the photoelectric element used as a visible light sensor of a solid state imaging device is required to achieve the highest possible photoelectric conversion efficiency and, in some cases, needs application of an external voltage in order to improve photoelectric conversion efficiency or response speed.

In the cases when an external voltage is applied for the purpose of improving photoelectric conversion efficiency or response speed, hole or electron injection from the electrode can occur, which may cause the problem of dark current increase.

Most of the materials generally used as electrodes of a photoelectric element are those having a work function of about 4.5 eV, such as indium tin oxide (ITO). When, for example, fullerene ($C_{60}$) is used as a material of a photoelectric layer, the energy gap between the work function of the electrode and the LUMO level of the fullerene ($C_{60}$) is small to allow charge carriers, particularly electrons, to be injected from the electrode into the photoelectric layer. This results in a considerable increase in dark current.

To prevent an increase of dark current due to charge carrier injection, JP 2008-72090A proposes providing a charge blocking layer for efficiently blocking injection of charges into a photoelectric layer thereby to reduce dark current.

However, JP 2007-123707A and JP 2008-72090A are silent to heat resistance, which is an important factor for practical use, giving no concrete description about the structural characteristics of compounds having high heat resistance.

A photoelectric element used in an imaging device must have high heat resistance, given that it is subjected to steps involving heating, such as color filter formation, protective film formation, and soldering, and also from the viewpoint of storage stability.

JP 2005-166637A discloses a triarylamine having a glass transition temperature (hereinafter "Tg") of 90° C. or higher for use to make an organic electroluminescence device. JP 7-324059A teaches a material having a Tg of around 70° C. for use to make an electrophotographic photoreceptor. However, either JP 2005-166637A or JP 7-324059A gives no mention regarding a photoelectric element.

JP 2005-32852A proposes using a substrate with a Tg of 80° C. or higher in an organic photoelectric element but does not refer to the characteristics of the materials used between electrodes, particularly a photoelectric layer material and a blocking layer material. There is no mention of a method for improving heat resistance of an organic photoelectric element in a very high temperature range, as high as 180° C. or higher, as referred to in the invention.

JP 2006-100508A and JP 2009-200482A discloses a photoelectric element having a photoelectric layer formed by co-deposition of a p type organic photoelectric material and a fullerene without specifically describing the characteristics of the material relevant to heat resistance.

SUMMARY OF INVENTION

An object of the invention is to provide a photoelectric element that achieves high external quantum efficiency, has low dark current, and exhibits sufficient heat resistance for withstanding heat treatment and minimizing reduction in external quantum efficiency and increase in dark current due to heat. Another object is to provide an imaging device having such a photoelectric element.

It is important for a material used in a photoelectric element to have not only high photoelectric conversion efficiency and low dark current but also performance stability throughout the processing steps in the manufacturing of the photoelectric element. The material is required to have good absorption characteristics to attain high photoelectric conversion efficiency and is limited in terms of ionization potential (hereinafter "IP") so as to perform separation of charges. A photoelectric element should have high heat resistance, given that it is subjected to steps involving heating, such as color filter formation, protective film formation, and soldering, and also from the viewpoint of storage stability.

For example, production of a full color imaging device involves formation of color filter layers. The processing temperature for making the color filters ranges from 180° to 220° C., while varying according to the specifications. That is, the photoelectric element must sufficiently withstand the temperature of 180° C. at the lowest. In the cases when an imaging device is soldered to a printed circuit board by solder reflow, which is economically advantageous, the photoelectric element is also required to be resistant to the soldering temperature.

The inventors of the present invention have studied the heat resistance of a photoelectric element. They have found, as a result, that a photoelectric element having layers made of materials whose glass transition temperatures are in specific ranges exhibits high heat resistance.

Providing a blocking layer produces good results for improving the performance of a photoelectric element. The materials making the blocking layer are limited in terms of absorption characteristics so as not to hinder light absorption by the photoelectric layer and also in terms of IP so as to allow transportation of charges generated in the photoelectric layer. From all these considerations, the inventors have found that a material having a specific structural characteristic is preferred to make a blocking layer. Similarly to the photoelectric layer material, the blocking layer material should have increased heat resistance. Among important factors deciding the heat resistance of the blocking layer material is a Tg.

As a result of intensive investigation, the inventors have found that the thermal characteristics, particularly the Tg, of materials making a photoelectric element are influential on the heat resistance of the element. Further investigation has revealed that a specific structural factor of the material contributes to the improvement on heat resistance. Hence, the object of the invention is accomplished by the provision of the following means.

The invention provides in its first aspect a photoelectric element including a conductive layer, an organic photoelectric layer, a blocking layer, and a transparent conductive layer. The organic photoelectric layer contains a p type organic photoelectric material having a Tg of 100° C. or higher and forming an amorphous layer. The blocking layer contains a blocking material having a Tg of 140° C. or higher.

The invention also provides a preferred embodiment of the photoelectric element, in which:
the blocking layer is an electron blocking layer;
the blocking material is a triarylamine;
the triarylamine is represented by formula (V):

Formula (V):

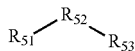

wherein $R_{51}$, $R_{52}$, and $R_{53}$ each independently represent a group containing an aryl group or a group containing a heteroaryl group, provided that at least one of $R_{51}$, $R_{52}$, and $R_{53}$ contains one nitrogen atom;
the blocking material has an IP of 4.7 to 5.8 eV;
the blocking material has an absorption maximum at a wavelength of 400 nm or shorter;
the p type organic photoelectric material is a p type organic semiconductor, and
the organic photoelectric layer is a mixture of the p type organic semiconductor and an n type organic semiconductor;
the p type organic photoelectric material has an absorption maximum in the wavelength range of from 450 nm to 620 nm and a molar extinction coefficient of 30,000 $M^{-1}cm^{-1}$ or more at the absorption maximum wavelength;
the p type organic photoelectric material has an IP of 4.5 to 5.8 eV; or
the p type organic photoelectric material is represented by formula (I):

Formula (I):

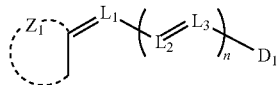

wherein $Z_1$ represents a ring structure containing at least two carbon atoms selected from a 5-membered ring, a 6-membered ring, and a fused ring having at least one of a 5-membered ring and a 6-membered ring; $L_1$, $L_2$, and $L_3$ each independently represent a methine group or a substituted methine group; $D_1$ represents an aryl group or a heteroaryl group; and n represents an integer of 0 or greater.

The invention provides in its second aspect an imaging device having the photoelectric element of the invention.

The invention provides in its third aspect a method for driving the photoelectric element of the invention or the photoelectric element used in the imaging device of the invention. The method includes applying an electric field of $1\times10^{-4}$ V/cm to $1\times10^7$ V/cm between the conductive layer and the transparent conductive layer serving as a pair of electrodes.

The invention also provides a preferred embodiment of the driving method, in which the electron blocking layer is in contact with one of the electrodes, and the electric field is applied with the electrode with which the electron blocking layer is in contact as a negative electrode and the opposing electrode as a positive electrode; or In another preferred embodiment of the driving method, light is allowed to impinge on the side of the electrode not being in contact with the electron blocking layer.

DESCRIPTION OF EMBODIMENTS

[Photoelectric Element]

Figure 1A:
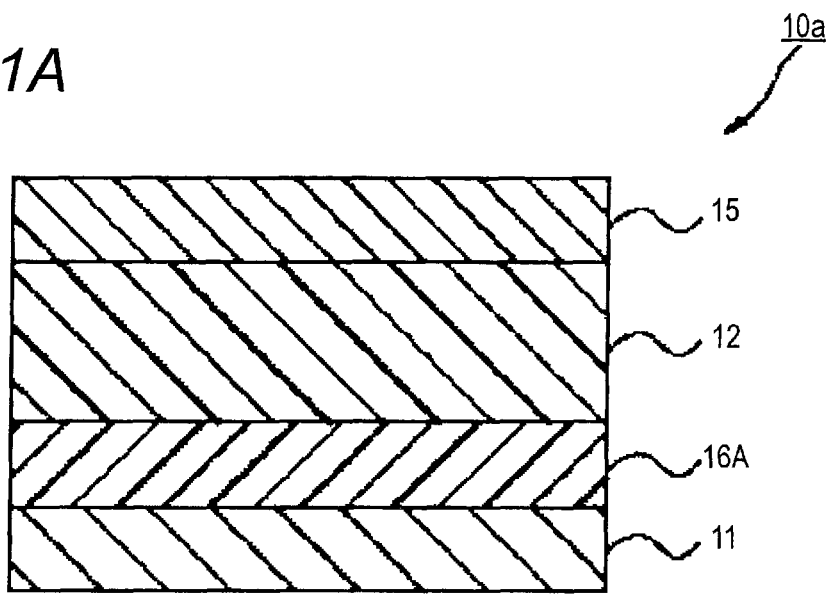
FIG. 1A and FIG. 1B are each a schematic cross-section of a photoelectric element.

The photoelectric element of the invention includes a conductive layer, an organic photoelectric layer, a blocking layer, and a transparent conductive layer. The organic photoelectric layer contains a p type organic photoelectric material having a Tg of 100° C. or higher and capable of forming an amorphous layer. The blocking layer contains a blocking material having a Tg of 140° C. or higher. Preferably, the photoelectric layer containing the p type organic photoelectric material and the blocking layer containing the blocking material are between the transparent conductive layer and the conductive layer.

A p type organic photoelectric material is a material having the character as a p type semiconductor and having hole transporting properties. It is a donating organic semiconductor (compound), i.e., an organic compound having electron donating character, which is mostly exemplified by a hole transporting organic compound. Any electron donating organic compound may serve as a p type organic photoelectric material. When an organic compound brought into contact with an n type semiconductor (e.g., a fullerene) is exposed to light with a voltage applied, if photoelectric conversion (conversion of light energy to electric energy) occurs, the organic compound is confirmed to have hole transporting properties.

Photoelectric materials of p type include crystalline materials that form a crystalline phase when fabricated into film (layer) and amorphous materials that form an amorphous phase when fabricated into film (layer). It is often the case that crystalline photoelectric materials suffer from change of crystalline phase, crystalline form, or film form when heated even below their melting temperature due to poor heat resistance. Furthermore, the crystal grain boundaries act as carrier traps, resulting in reduced photoelectric conversion efficiency and increased dark current. On the other hand, amorphous materials are easy to form into smooth film (smooth layer) and basically do not change until the heating temperature reaches the Tg. Therefore, the p type organic photoelectric material used in the invention is an amorphous material forming an amorphous layer. To secure heat resistance, the Tg of the p type organic photoelectric material is 100° C. or higher, preferably 120° C. or higher, more preferably 140° C. or higher. The upper limit of the Tg is preferably 350° C., more preferably 300° C., which may be reached by practically available materials. Whether a p type organic photoelectric material forms an amorphous film depends on the material, method of film formation, and film formation conditions.

Since the p type organic photoelectric material should absorb light and convert the absorbed light to charges, it is required to have sufficient absorption characteristics. In this regard, the p type organic photoelectric material preferably has an absorption maximum wavelength in the range of from 450 to 620 nm, more preferably 470 to 600 nm, even more preferably 500 to 580 nm, and a molar extinction coefficient at that wavelength of 30,000 $M^{-1}cm^{-1}$ or more, more preferably 30,000 to 400,000 $M^{-1}cm^{-1}$, even more preferably 40,000 to 200,000 $M^{-1}cm^{-1}$, most preferably 50,000 to 100,000 $M^{-1}cm^{-1}$.

It is particularly preferred for the p type organic photoelectric material to have an absorption maximum wavelength of 450 to 620 nm and a molar extinction coefficient at the absorption maximum wavelength of 30000 $M^{-1}cm^{-1}$ or more.

There is a preferred range of ionization potential (IP) for the p type organic photoelectric material. The IP of the material in the form of a film (layer) is preferably 4.5 to 5.8 eV, more preferably 4.7 to 5.7 eV, even more preferably 4.8 to 5.6 eV. This is because, when the difference between the electron level of the material and the work function of the electrode is small, the electric field intensity required for charge transfer is small.

As regards the structural factor, a p type organic photoelectric material having an aromatic ring (e.g., a benzene ring, a furan ring, a thiophene ring, a selenophene ring, a silol ring, a pyridine ring, a pyrazine ring, a pyrimidine ring, an oxazole ring, a thiazole ring, a triazole ring, an oxadiazole ring, or a thiadiazole ring), especially a benzene ring, as a part of a fused ring structure exhibits high heat resistance.

The p type organic photoelectric material is, as mentioned above, a donating organic semiconductor (compound), i.e., an organic compound having electron donating character, which is mostly exemplified by a hole transporting organic compound. In some detail, when two organic materials are used in contact with each other, the material having a smaller ionization potential is an electron donating compound. Any electron donating organic compound may be used, including triarylamine compounds, benzidine compounds, pyrazoline compounds, styrylamine compounds, hydrazone compounds, triphenylmethane compounds, carbazole compounds, polysilane compounds, thiophene compounds, phthalocyanine compounds, cyanine compounds, merocyanine compounds, oxonol compounds, polyamine compounds, indole compounds, pyrrole compounds, pyrazole compounds, polyarylene compounds, fused aromatic carbocyclic compounds (e.g., naphthalene derivatives, anthracene derivatives, phenanthrene derivatives, tetracene derivatives, pyrene derivatives, perylene derivatives, and fluoranthene derivatives), and metal complexes having a nitrogen-containing heterocyclic compound as a ligand. In addition, any organic compounds having a smaller IP than an organic compound used as an n type, electron-accepting organic compound may be used as a donating organic semiconductor.

Examples of the p type organic photoelectric material include the colorants described in JP 2006-86157A, JP 2006-86160A, JP 2006-100502A, JP 2006-100508A, JP 2006-100767A, JP 2006-339424A, JP 2008-244296A, and JP 2009-088291A.

The p type organic photoelectric material is preferably represented by formula (I):

Formula (I):

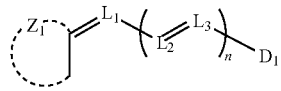

wherein $Z_1$ represents a ring structure containing at least two carbon atoms selected from a 5-membered ring, a 6-membered ring, and a fused ring having at least one of a 5-membered ring and a 6-membered ring; $L_1$, $L_2$, and $L_3$ each independently represent a substituted or unsubstituted methine group; $D_1$ represents an aryl group or a heteroaryl group; and n represents an integer of 0 or greater.

$Z_1$ represents a ring structure containing at least two carbon atoms selected from a 5-membered ring, a 6-membered ring, and a fused ring having at least one of a 5-membered ring and a 6-membered ring. The 5- or 6-membered ring or the fused ring containing at least one of a 5-membered ring and a 6-membered ring as represented by $Z_1$ is preferably an acidic nuclei generally used in merocyanine dyes. Examples of such rings include:
(a) 1,3-dicarbonyl nuclei, such as 1,3-indandione, 1,3-cyclohexanedione, 5,5-dimethyl-1,3-cyclohexanedione, and 1,3-dioxane-4,6-dione,
(b) pyrazolinone nuclei, such as 1-phenyl-2-pyrazolin-5-one, 3-methyl-1-phenyl-2-pyrazolin-5-one, and 1-(2-benzothiazolyl)-3-methyl-2-pyrazolin-5-one,
(c) isoxazolinone nuclei, such as 3-phenyl-2-isoxazolin-5-one and 3-methyl-2-isoxazolin-5-one,
(d) oxyindole nuclei, such as 1-alkyl-2,3-dihydro-2-oxyindole,
(e) 2,4,6-triketohexahydropyrimidine nuclei, such as barbituric acid, 2-thiobarbituric acid, and derivatives thereof including 1-alkyl (e.g., 1-methyl or 1-ethyl) derivatives, 1,3-dialkyl (e.g., 1,3-diethyl or 1,3-dibutyl) derivatives, 1,3-diaryl (e.g., 1,3-diphenyl, 1,3-di(p-chlorophenyl), or 1,3-di(p-ethoxycarbonylphenye) derivatives, 1-alkyl-3-aryl (e.g., 1-ethyl-3-phenyl) derivatives, and 1,3-di(hetero ring) (e.g., 1,3-di(2-pyridyl)) derivatives,
(f) 2-thio-2,4-thiazolidinedione nuclei, such as rhodanine and its derivatives including 3-alkylrhodanines (e.g., 3-methylrhodanine, 3-ethylrhodanine, and 3-allylrhodanine), 3-arylrhodanines (e.g., 3-phenylrhodanine), and 3-(hetero ring)rhodanines (e.g., 3-(2-pyridyl)rhodanine),
(g) 2-thio-2,4-oxazolidinedione (or 2-thio-2,4-(3H,5H)-oxazoledione) nuclei, such as 3-ethyl-2-thio-2,4-oxazolidinedione,
(h) thianaphthenone nuclei, such as 3(2H)-thianaphthenone 1,1-dioxide,
(i) 2-thio-2,5-thiazolidinedione nuclei, such as 3-ethyl-2-thio-2,5-thiazolidinedione,
(j) 2,4-thiazolidinedione nuclei, such as 2,4-thiazolidinedione, 3-ethyl-2,4-thiazolidinedione, and 3-phenyl-2,4-thiazolidinedione,
(k) thiazolin-4-one nuclei, such as 4-thiazolinone and 2-ethyl-4-thiazolinone,
(l) 2,4-imidazolidinedione (or hydantoin) nuclei, such as 2,4-imidazolidinedione and 3-ethyl-2,4-imidazolidinedione, (m) 2-thio-2,4-imidazolidinedione (or 2-thiohydantoin) nuclei, such as 2-thio-2,4-imidazolidinedione and 3-ethyl-2-thio-2,4-imidazolidinedione, (n) imidazolin-5-one nuclei, such as 2-propylmercapto-2-imidazolin-5-one, (o) 3,5-pyrazolidinedione nuclei, such as 1,2-diphenyl-3,5-pyrazolidinedione and 1,2-dimethyl-3,5-pyrazolidinedione, (p) benzothiophen-3-one nuclei, such as benzothiophen-3-one, oxobenzothiophen-3-one, and dioxobenzothiophen-3-one, and (q) indanone nuclei, such as 1-indanone, 3-phenyl-1-indanone, 3,3-diphenyl-1-indanone, and 3,3-dimethyl-1-indanone.

The ring structure represented by $Z_1$ is preferably a 1,3-dicarbonyl nucleus, a pyrazolinone nucleus, a 2,4,6-triketohexahydropyrimidine nucleus (including a thioketone form), such as a barbituric acid nucleus or a 2-thiobarbituric acid nucleus, a 2-thio-2,4-thiazolidinedione nucleus, 2-thio-2,4-oxazolidinedione nucleus, a 2-thio-2,5-thiazolidinedione nucleus, a 2,4-thiazolidinedione nucleus, a 2,4-imidazolidinedione nucleus, a 2-thio-2,4-imidazolidinedione nucleus, a 2-imidazolin-5-one nucleus, a 3,5-pyrazolidinedione nucleus, a benzothiophen-3-one nucleus, or a indanone nucleus; more preferably a 1,3-dicarbonyl nucleus, a 2,4,6-triketohexahydropyrimidine nucleus (including a thioketone form), such as a barbituric acid nucleus or a 2-thiobarbituric acid nucleus, a 3,5-pyrazolidinedione nucleus, a benzothiophen-3-one nucleus, or an indanone nucleus; even more preferably a 1,3-dicarbonyl nucleus, a 2,4,6-triketohexahydropyrimidine nucleus (including a thioketone form), such as a barbituric acid nucleus or a 2-thiobarbituric acid nucleus; most preferably a 1,3-indanedione nucleus, a barbituric acid nucleus, a 2-thiobarbituric acid nucleus, or a derivative thereof.

The acid nuclei described may further have a 5- or 6-membered ring fused thereto. For example, a 1,3-indanedione nucleus may have a 5- or 6-membered ring fused thereto. It is also preferred for a 1,3-indanedione nucleus to have a 6-membered ring (e.g., benzene ring) fused to the 5,6-positions thereof.

$L_1$, $L_2$, and $L_3$ each independently represent a methine group or a substituted methine group. The substituted methine groups represented by $L_1$, $L_2$, and $L_3$ may be taken together to form a ring, such as a 6-membered ring (e.g., a benzene ring). Examples of the substituent of the substituted methine group include those designated "substituent(s) W" as enumerated infra. It is preferred that all of $L_1$, $L_2$, and $L_3$ be an unsubstituted methine group.

$L_1$, $L_2$, and $L_3$ may be taken together to form a ring. Preferred examples of the ring formed include cyclohexene, cyclopentene, benzene, naphthalene, thiophene, and pyran.

Symbol n represents an integer of 0 or greater. It is preferably 0 to 3, more preferably 0. As the number n increases, the absorption wavelength range extends to the side of longer wavelengths, but the thermal decomposition temperature decreases. In order to secure appropriate absorption in the visible region while preventing thermal decomposition during vapor deposition, n is preferably 0.

$D_1$ represents an aryl group or a heteroaryl group. An aryl group is preferred to a heteroaryl group. $D_1$ is preferably a group containing —$NR^a(R^b)$ wherein $R^a$ and $R^b$ each represent a hydrogen atom or a substituent. $D_1$ is more preferably an aryl group substituted with —$NR^a(R^b)$.

The aryl group as represented by $D_1$ preferably has 6 to 30, more preferably 6 to 18, carbon atoms. The aryl group may have a substituent W. The aryl group is preferably a C6 to C18 aryl group (an aryl group having 6 to 18 carbon atoms) that may have a C1 to C4 alkyl group. $D_1$ is preferably phenyl, naphthyl, anthracenyl, pyrenyl, phenanthrenyl, methylphenyl, or a dimethylphenyl, with phenyl or naphthyl being more preferred.

The heteroaryl group as represented by $D_1$ preferably has 3 to 30, more preferably 4 to 18, carbon atoms. The heteroaryl group may have a substituent W. The heteroaryl group is preferably a C4 to C18 heteroaryl group that may have a C1 to C4 alkyl group. Preferred examples of the heteroaryl structure include thiophene, furan, pyrrole, oxazole, diazole, and thiazole, each of which may be fused to a benzene or thieno ring. More preferred are thiophene, benzothiophene, thienothiophene, dibenzothiophene, and bithienothiophene.

Examples of the substituent as $R^a$ or $R^b$ include substituents W, preferably aliphatic hydrocarbon groups (particularly substituted or unsubstituted alkyl or alkenyl), aryl groups (particularly substituted or unsubstituted phenyl), and heterocyclic groups.

Each of the aryl groups as represented by $R^a$ and $R^b$ preferably has 6 to 30, more preferably 6 to 18, carbon atoms and may have a substituent. The aryl group is more preferably a C6 to C18 aryl group which may have a C1 to C4 alkyl or a C6 to C18 aryl group, such as phenyl, naphthyl, anthracenyl, pyrenyl, phenanthrenyl, methylphenyl, dimethylphenyl, or biphenyl. Phenyl, naphthyl, or anthracenyl is particularly preferred.

Each of the heterocyclic groups as represented by $R^a$ and $R^b$ preferably has 3 to 30, more preferably 3 to 18, carbon atoms and may have a substituent. The heterocyclic group is preferably a C3 to C18 heterocyclic group which may have a C1 to C4 alkyl or a C6 to C18 aryl group. The heterocyclic group preferably has a fused ring structure. The fused ring structure is preferably composed of rings selected from benzene, furan, thiophene, selenophene, silol, pyridine, pyrazine, pyrimidine, oxazole, thiazole, triazole, oxadiazole, and thiadiazole rings. The rings composing the fused ring structure may be the same or different, provided that a combination of benzene rings is excluded. Preferred examples of the fused ring structure are quinoline, isoquinoline, benzothiophene, dibenzothiophene, thienothiophene, bithienobenzene, and bithienothiophene.

The aryl group as represented by $D_1$, $R^a$, or $R^b$ is preferably a fused ring structure, more preferably a fused ring structure containing a benzene ring, even more preferably a naphthalene, anthracene, pyrene, or phenanthrene ring, most preferably a naphthalene or anthracene ring.

Examples of substituents W include halogen, alkyl (including cycloalkyl, bicycloalkyl, and tricycloalkyl), alkenyl (including cycloalkenyl and bicycloalkenyl), alkynyl, aryl, heterocyclic (hetero ring), cyano, hydroxyl, nitro, carboxyl, alkoxy, aryloxy, silyloxy, heterocyclic oxy, aryloxy, carbamoyloxy, alkoxycarbonyl, aryloxycarbonyl, amino (including anilino), ammonio, acylamino, aminocarbonylamino, alkoxycarbonylamino, aryloxycarbonylamino, sulfamoylamino, alkylsulfonylamino, arylsulfonylamino, mercapto, alkylthio, arylthio, heterocyclic thio, sulfamoyl, sulfo, alkylsulfinyl, arylsulfinyl, alkylsulfonyl, arylsulfonyl, acyl, aryloxycarbonyl, alkoxycarbonyl, carbamoyl, arylazo, heterocyclic azo, imido, phosphino, phosphinyl, phosphinyloxy, phosphinylamino, phosphono, silyl, hydrazino, ureido, boronic acid (—$B(OH)_2$), phosphate (—$OPO(OH)_2$), sulfato (—$OSO_3H$), and other known substituents.

When $R^a$ or $R^b$ is an aliphatic hydrocarbon group (preferably alkyl or alkenyl), the aliphatic hydrocarbon group may be connected to the hydrogen atom or substituent of the aromatic ring (preferably a benzene ring) of the aryl group substituted with —NR$^a$(R$^b$) to form a ring, preferably a 6-membered ring.

When R$^a$ and R$^b$ are both a substituent, they may be connected to each other to form a ring, preferably 5- or 6-membered ring, more preferably a 6-membered ring, or each of them may be connected to the substituent of any one of L$_1$, L$_2$, and L$_3$ to form a ring, preferably 5- or 6-membered ring, more preferably a 6-membered ring.

The compounds represented by formula (I) are identical to those described in JP 2000-297068A. The compounds of formula (I), whether or not specifically described in JP 2000-297068A, can be produced in accordance with the process described therein.

The compounds of formula (I) are preferably represented by formula (II):

Formula (II):

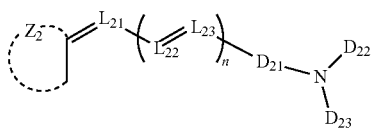

wherein Z$_2$, L$_{21}$, L$_{22}$, L$_{23}$, and n have the same meanings and the same preferred meanings as Z$_1$, L$_1$, L$_2$, L$_3$, and n, respectively, in formula (I); D$_{21}$ represents a substituted or unsubstituted arylene group; and D$_{22}$ and D$_{23}$ each independently represent a substituted or unsubstituted aryl group or a substituted or unsubstituted heterocyclic group.

The arylene group as represented by D$_{21}$ preferably has 6 to 30, more preferably 6 to 18, carbon atoms. The arylene group may have the above-mentioned substituent W. The arylene group is preferably a C6 to C18 arylene group that may have a C1 to C4 alkyl group, such as phenylene, naphthylene, anthracenylene, pyrenylene, phenanthrenylene, methylphenylene, or a dimethylphenylene. The arylene group is more preferably phenylene or naphthylene.

D$_{22}$ and D$_{23}$ each preferably independently represent a fused aromatic ring. The fused aromatic ring structure is preferably composed of rings, which may be the same or different, selected from benzene, furan, thiophene, selenophene, silol, pyridine, pyrazine, pyrimidine, oxazole, thiazole, triazole, oxadiazole, and thiadiazole rings. Preferred examples of the fused ring structure are naphthalene, anthracene, pyrene, phenanthrene, quinoline, isoquinoline, benzothiophene, dibenzothiophene, thienothiophene, bithienobenzene, and bithienothiophene.

The aryl group as represented by D$_{22}$ or D$_{23}$ preferably has a fused ring structure, more preferably a fused ring structure containing a benzene ring, even more preferably a benzene, naphthalene, anthracene, pyrene, or phenanthrene ring, most preferably a naphthalene or anthracene ring. The heterocyclic group as represented by D$_{22}$ or D$_{23}$ preferably has a fused ring structure, more preferably a fused ring structure composed of rings selected from benzene, furan, thiophene, selenophene, silol, pyridine, pyrazine, pyrimidine, oxazole, thiazole, triazole, oxadiazole, and thiadiazole rings. The rings composing the fused ring structure may be the same or different, provided that a combination of benzene rings is excluded. Preferred examples of the fused ring structure are quinoline, isoquinoline, benzothiophene, dibenzothiophene, thienothiophene, bithienobenzene, and bithienothiophene.

Specific but non-limiting examples of preferred compounds of formula (I) are shown below by way of formula (III):

Formula (III):

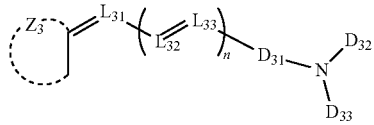

wherein Z$_3$ is any one of A-1 through A-12 shown in Table 1; L$_{31}$ is a methine group; n is 0; D$_{31}$ is any one of B-1 through B-9 shown in Table 1; and each of D$_{32}$ and D$_{33}$ is any one of C-1 through C-16 shown in Table 1. In Table 1, the asterisk (*) indicates the position of bonding to L$_{31}$ or L$_{33}$.

TABLE 1

| | |
|---|---|
| 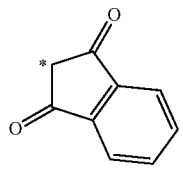 [SMILES: O=C1CC(=O)c2ccccc21] | A-1 |
| 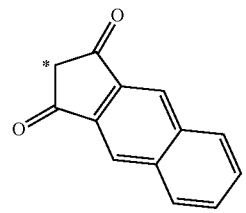 [SMILES: O=C1CC(=O)c2cc3ccccc3cc21] | A-2 |
| 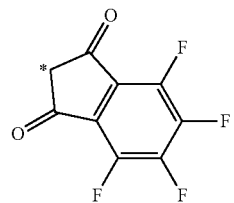 [SMILES: O=C1CC(=O)c2c(F)c(F)c(F)c(F)c21] | A-3 |
| 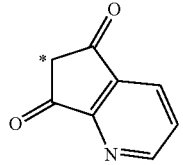 [SMILES: O=C1CC(=O)c2ncccc21] | A-4 |
| 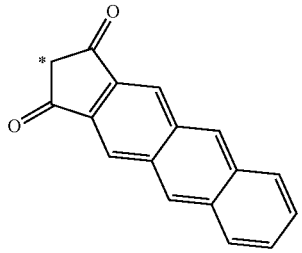 [SMILES: O=C1CC(=O)c2cc3cc4ccccc4cc3cc21] | A-5 |

TABLE 1-continued

| Label | | Label |
|---|---|---|
| A-6 | (barbituric acid structure) | B-2 (naphthalene) |
| A-7 | (thiobarbituric acid structure) | B-3 (anthracene) |
| A-8 | (1,3-dimethylbarbituric acid) | B-4 (benzothiophene) |
| A-9 | (1,3-cyclohexanedione) | B-5 (thienothiophene) |
| A-10 | (chroman-2,4-dione) | B-6 (dithienothiophene) |
| A-11 | (N-methyl benzo[f]quinoline-1,3-dione) | B-7 (dibenzothiophene) |
| A-12 | (1,3-diphenylpyrazol-5-one) | B-8 (benzodithiophene) |
| B-1 | (naphthalene) | B-9 (benzene) |
| | | C-1 (naphthalene) |
| | | C-2 (naphthalene) |
| | | C-3 (anthracene) |
| | | C-4 (anthracene) |
| | | C-5 (phenanthrene) |

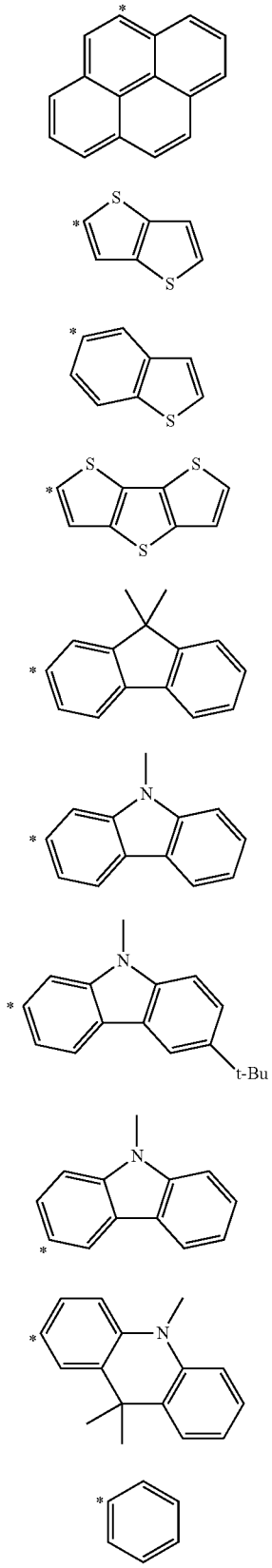

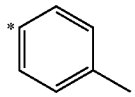

More specific examples of the p type photoelectric materials of formula (I) include, but are not limited to, the combinations of substituents, linking group, and partial structure shown in Table 2, in which A-1 to A-12, B-1 to B-9, and C-1 to C-16 are the same as in Table 1.

TABLE 2

| Compound No. | $Z_3$ | $L_{31}$ | n | $D_{31}$ | $D_{32}$ | $D_{33}$ |
|---|---|---|---|---|---|---|
| 1 | A-1 | CH | 0 | B-9 | C-1 | C-1 |
| 2 | A-2 | CH | 0 | B-9 | C-15 | C-15 |
| 3 | A-3 | CH | 0 | B-9 | C-15 | C-15 |
| 4 | A-4 | CH | 0 | B-9 | C-15 | C-15 |
| 5 | A-5 | CH | 0 | B-9 | C-15 | C-15 |
| 6 | A-10 | CH | 0 | B-9 | C-15 | C-15 |
| 7 | A-11 | CH | 0 | B-9 | C-15 | C-15 |
| 8 | A-6 | CH | 0 | B-1 | C-15 | C-15 |
| 9 | A-7 | CH | 0 | B-1 | C-15 | C-15 |
| 10 | A-8 | CH | 0 | B-1 | C-15 | C-15 |
| 11 | A-9 | CH | 0 | B-1 | C-15 | C-15 |
| 12 | A-12 | CH | 0 | B-1 | C-15 | C-15 |
| 13 | A-2 | CH | 0 | B-2 | C-15 | C-15 |
| 14 | A-2 | CH | 0 | B-3 | C-15 | C-15 |
| 15 | A-2 | CH | 0 | B-4 | C-15 | C-15 |
| 16 | A-2 | CH | 0 | B-5 | C-15 | C-15 |
| 17 | A-2 | CH | 0 | B-6 | C-15 | C-15 |
| 18 | A-2 | CH | 0 | B-7 | C-15 | C-15 |
| 19 | A-2 | CH | 0 | B-8 | C-15 | C-15 |
| 20 | A-2 | CH | 0 | B-1 | C-1 | C-1 |
| 22 | A-2 | CH | 0 | B-1 | C-1 | C-3 |
| 23 | A-2 | CH | 0 | B-9 | C-15 | C-4 |
| 24 | A-2 | CH | 0 | B-9 | C-15 | C-5 |
| 25 | A-2 | CH | 0 | B-9 | C-15 | C-6 |
| 26 | A-2 | CH | 0 | B-9 | C-7 | C-7 |
| 27 | A-2 | CH | 0 | B-9 | C-8 | C-8 |
| 28 | A-2 | CH | 0 | B-1 | C-10 | C-10 |
| 29 | A-2 | CH | 0 | B-9 | C-11 | C-11 |
| 30 | A-2 | CH | 0 | B-9 | C-12 | C-12 |
| 31 | A-2 | CH | 0 | B-9 | C-15 | C-1 |
| 32 | A-2 | CH | 0 | B-9 | C-16 | C-16 |

[Organic Photoelectric Layer]

It is preferred for the organic photoelectric layer containing the p type organic photoelectric material to further contain an n type organic photoelectric material (hereinafter "n type organic semiconductor"). It is more preferred that the p type organic photoelectric material be a p type organic semiconductor and that the organic photoelectric layer be a mixed layer containing the p type organic semiconductor and an n type organic semiconductor. In such a mixed layer, pn junctions exist within distances (generally 3 to 10 nm) that the photogenerated excitons are able to travel so that the excitons are efficiently dissociated into positive and negative charges before being deactivated, resulting in achievement of high photoelectric efficiency.

The organic n type semiconductor (compound) is an accepting organic semiconductor (compound), i.e., an organic compound having electron accepting character, which is mostly exemplified by an electron transporting organic compound. In some detail, when two organic compounds are used in contact with each other, the compound having larger electron affinity is an electron accepting compound. Any compound having electron accepting character may be used, including fused aromatic carbocyclic compounds (e.g., naphthalene, anthracene, fullerenes, phenanthrene, tetracene, pyrene, perylene, fluoranthene, and their derivatives), nitrogen-, oxygen- or sulfur-containing 5- to 7-membered heterocyclic compounds (e.g., pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, thiazole, oxazole, indazole, benzimidazole, benzotriazole, benzoxazole, benzothiazole, carbazole, purine, triazolopyridazine, triazolopyrimidine, tetraazaindene, oxadiazole, imidazopyridine, pyralidine, pyrrolopyridine, thiadiazolopyridine, dibenzazepin, and tribenzazepin), polyarylene compounds, fluorene compounds, cyclopentadiene compounds, silyl compounds, and metal complexes having a nitrogen-containing heterocyclic compound as a ligand. In addition, any organic compounds having larger electron affinity than an organic compound used as an electron-donating organic compound may be used as an accepting organic semiconductor.

The n type organic semiconductor is preferably a compound having an electron affinity of 3.4 to 5.2 eV, more preferably a compound having an electron affinity of 3.9 to 4.5 eV, even more preferably a fullerene or a fullerene derivative.

Examples of fullerenes include fullerene $C_{60}$, $C_{70}$, $C_{76}$, $C_{78}$, $C_{80}$, $C_{82}$, $C_{84}$, $C_{90}$, $C_{96}$, $C_{82}$, $C_{84}$, $C_{90}$, $C_{96}$, $C_{240}$, and $C_{540}$, mixed fullerenes, and fullerene nanotubes. Fullerene derivatives are compounds derived from the fullerenes by addition of a substituent, such as an alkyl group, an aryl group, or a heterocyclic group. The fullerene derivatives described in JP 2007-123707A are preferred.

The compounds described in The Chemical Society of Japan (ed.), *Quarterly Chemical Reviews* No. 43 (1999), JP 10-167994A, JP 11-255508A, JP 11-255509A, JP 2002-241323A, and JP 2003-196881A are also useful.

The content of a fullerene or a fullerene derivative in the mixed layer is preferably at least 50%, more preferably 200% or more, even more preferably 300% or more, by mole with respect to the other materials forming the mixed layer.

The organic photoelectric layer may be formed by a solution process but is preferably formed by vapor deposition, such as physical vapor deposition (PVD) or chemical vapor deposition (CVD), in terms of device performance. PVD is preferred to CVD. In the case of vacuum deposition, the degree of vacuum, the deposition temperature, and other deposition conditions may be decided in a usual manner.

The organic photoelectric layer preferably has a thickness of 10 to 1000 nm, more preferably 50 to 800 nm, even more preferably 100 to 500 nm. Thicknesses of 10 nm or greater are effective in preventing dark current generation. Good photoelectric conversion efficiency is obtained with thicknesses of 1000 nm or smaller.

[Blocking Layer]

In a preferred embodiment, the photoelectric element has a conductive layer, an organic photoelectric layer, and a transparent conductive layer stacked in the order described with a blocking layer interposed between the transparent conductive layer or the conductive layer and the photoelectric layer. This layer structure is preferred to further reduce dark current. The blocking layer is preferably a hole blocking layer or an electron blocking layer.

The blocking material used to form the blocking layer has a Tg of 140° C. or higher, more preferably 170° C. or higher, even more preferably 200° C. or higher. The higher the Tg of the blocking material, the higher the heat resistance of the photoelectric element. When in using the blocking material with a Tg of 200° C. or higher, the photoelectric element experiences performance improvements rather than deterioration on being heated. The Tg is determined using a differential scanning calorimeter. Using a blocking material with a Tg of 140° C. or higher to form the blocking layer makes the photoelectric element more heat resistant. The upper limit of the Tg is preferably 350° C., more preferably 300° C., which may be reached by practically available materials.

It is necessary that the blocking material not substantially absorb visible light. If the blocking material absorbs light that should be made use of for photoelectric conversion, it will hinder photoelectric conversion. The absorption maximum wavelength of the blocking material is preferably 400 nm or shorter, more preferably 390 nm or shorter, even more preferably 380 nm or shorter. When the electron blocking material has an absorption maximum at a wavelength in the visible region (i.e., 400 to 800 nm), the molar extinction coefficient of the material at the wavelength is preferably 0 to 5000 $M^{-1}cm^{-1}$, more preferably 0 to 3000 $M^{-1}cm^{-1}$, even more preferably 0 to 1000 $M^{-1}cm^{-1}$. The smaller the molar extinction coefficient, the more preferred.

[Electron Blocking Layer]

Providing an electron blocking layer is preferred to providing a hole blocking layer. Both an electron blocking layer and a hole blocking layer may be provided.

The conductive layer and the transparent conductive layer serve as a pair of electrodes. The electron blocking layer is preferably provided in contact with either one of the electrodes. The electrode with which the electron blocking layer is in contact preferably functions as a negative electrode. The electrode with which the electron blocking layer is in contact is preferably a conductive layer.

In order to transport signal charge from the photoelectric layer, the blocking material should have a relatively lower oxidation potential than the photoelectric material and a small IP. The IP of the blocking material in the form of a film (layer) is preferably 4.7 to 5.8 eV, more preferably 4.8 to 5.7 eV, further more preferably 4.9 to 5.6 eV, still further more preferably 5.5 to 5.6 eV.

Useful electron blocking materials are exemplified by aromatic hydrocarbon compounds and complex compounds each satisfying the above discussed characteristics. Triarylamines are preferred. The hole transporting materials described in *Chemical Review*, vol. 107, p. 953, 2007 and the compounds described in JP 2007-59517A are particularly preferred. Any other known or noble electron blocking materials are usable.

Of triarylamine blocking materials, preferred are those represented by formula (IV) shown below to satisfy the above discussed characteristics.

Formula (IV):

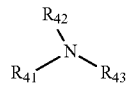

wherein $R_{41}$, $R_{42}$, and $R_{43}$ each independently represent an aryl group or a heteroaryl group.

Each of $R_{41}$, $R_{42}$, and $R_{43}$ preferably contains 4 to 48 carbon atoms, more preferably 5 to 36 carbon atoms.

Preferred examples of the aryl group as $R_{41}$, $R_{42}$, and $R_{43}$ include phenyl, naphthyl, anthryl, pyrenyl, phenanthryl, and fluorenyl, with phenyl, anthryl, and fluorenyl being more preferred, and with phenyl and fluorenyl being even more preferred.

Preferred examples of the heteroaryl group as $R_{41}$, $R_{42}$, and $R_{43}$ include pyrrole, furan, thiophenyl, pyridyl, pyrimidyl, and their benzo and naphtho derivatives, with pyrrole and thiophenyl being more preferred, and with those substituted with alkyl or aryl being even more preferred.

The aryl or heteroaryl group as $R_{41}$, $R_{42}$, and $R_{43}$ may be substituted with an amino group derived from the triarylamine represented by formula (IV).

$R_{41}$, $R_{42}$, and $R_{43}$ are preferably connected to each other by a single bond or via a C1-C3 alkylene group, a C6-C18 arylene group, or a C4-C18 heteroarylene group. It is more preferred that two of $R_{41}$, $R_{42}$, and $R_{43}$ be taken together to form a carbazolyl group, even more preferably an alkyl- or aryl-substituted carbazolyl group.

Specific examples of the triarylamines of formula (IV) are shown below.

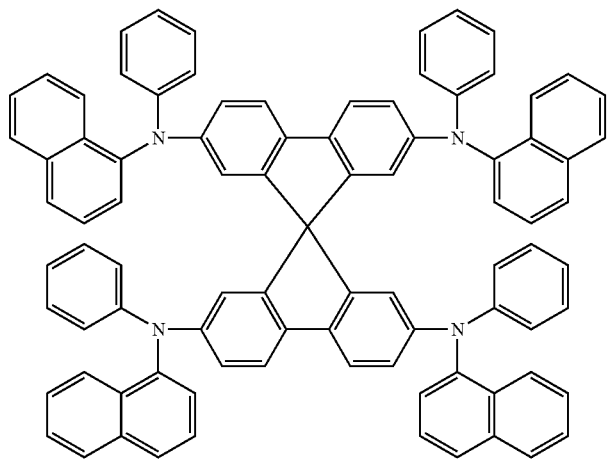

spiro-1-NBP

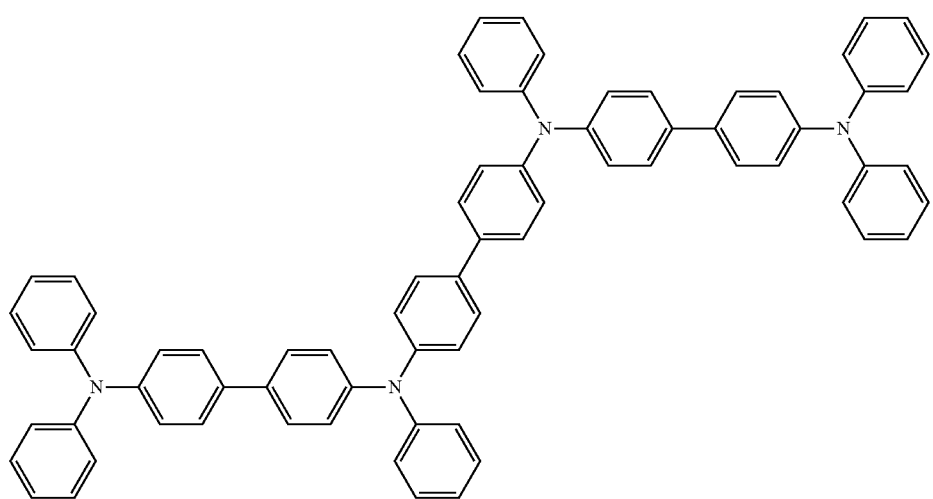

TPT-1

-continued

TBFABT

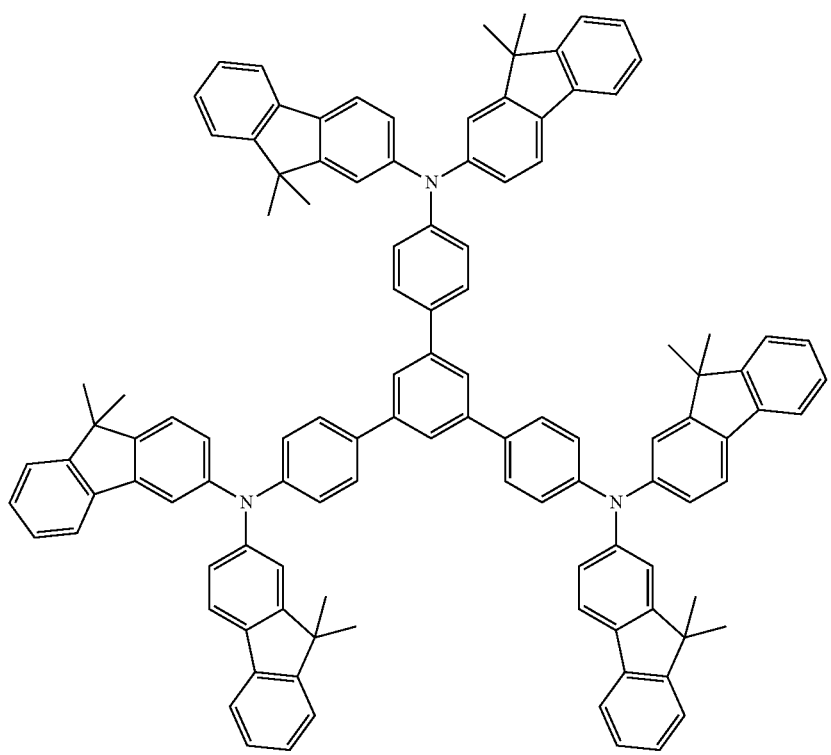

The triarylamine that can be used in the invention may be synthesized by known processes, such as Suzuki coupling, Ullmann coupling, or palladium amination.

The amount of the electron blocking material to be used is preferably such as to provide a single layer with a thickness of 10 to 300 nm, more preferably 30 to 150 nm, even more preferably 50 to 120 nm. Reduction of dark current is sufficiently exhibited with the electron blocking layer thickness of 10 nm or greater. With the thickness being 300 nm or smaller, reduction in photoelectric conversion efficiency is suppressed. The electron blocking layer is preferably provided as a single layer but may be divided into sublayers.

Of the triarylamine electron blocking materials, more preferred are those represented by formula (V):

Formula (V):

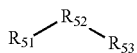

wherein $R_{51}$, $R_{52}$, and $R_{53}$ each independently represent a group containing an aryl group or a group containing a heteroaryl group, provided that at least one of $R_{51}$, $R_{52}$, and $R_{53}$ contains one nitrogen atom.

Each of $R_{51}$, $R_{52}$, and $R_{53}$ preferably contains 4 to 48 carbon atoms, more preferably 5 to 36 carbon atoms.

Each of $R_{51}$ and $R_{53}$ is preferably a fused ring structure having at least three rings which may be the same or different. Preferred combinations of the rings include 6-membered ring/5-membered ring/6-membered ring, 6-membered ring/6-membered ring/6-membered ring, and 6-membered ring/7-membered ring/6-membered ring, with 6-membered ring/5-membered ring/6-membered ring being more preferred. It is preferred for all these rings be unsaturated. The 6-membered ring is preferably a benzene, pyridine, or pyrimidine ring. The 5-membered ring is preferably a pyrrole, cyclopentene, furan, or thiophene ring. The 7-membered ring is preferably an azepine ring.

Each of $R_{51}$ and $R_{53}$ is preferably phenyl, naphthyl, anthryl, fluorenyl, phenanthryl, carbazolyl, dibenzofuryl, dibenzothionyl, acridinyl, or dibenzoazepinyl, with fluorenyl, phenanthryl, carbazolyl, dibenzofuryl, acridinyl, or dibenzoazepinyl being more preferred, with fluorenyl, carbazolyl, acridinyl, or dibenzoazepinyl being even more preferred, and with carbazolyl or acridinyl being most preferred.

These rings may be substituted with the above described substituent W, preferably alkyl or aryl. The alkyl preferably contains 1 to 10, more preferably 3 to 6, carbon atoms. The aryl preferably contains 6 to 18, more preferably 6 to 12, carbon atoms. A t-butyl group and a benzo group (to be fused to form a fused ring) are particularly preferred substituents. Two or more substituents may be taken together to form a ring structure.

$R_{52}$ is preferably a single bond, —N—$R_{54}$ (wherein $R_{54}$ is a substituent), or any one of the fused rings having at least three rings that are enumerated above as preferred examples of $R_{51}$ and $R_{53}$. The substituent as $R_{54}$ may be the substituent W, and is preferably alkyl or aryl, more preferably aryl.

Preferred examples of $R_{54}$ include phenyl, naphthyl, anthryl, fluorenyl, phenanthryl, carbazolyl, dibenzofuryl, and dibenzothionyl, with phenyl, naphthyl, anthryl, and fluorenyl being more preferred. $R_{54}$ preferably has an alkyl or aryl substituent.

When $R_{52}$ is a fused ring structure having at least three rings, preferred examples of the fused ring structure are the same as those enumerated above as preferred examples of $R_{51}$ and $R_{53}$. In particular, a bis-form of any one of the enumerated fused rings or any one of the enumerated fused rings to which —N—$R_{54}$ is bonded is especially preferred as $R_{52}$.

In formula (V), it is preferred that each of $R_{51}$, $R_{52}$, and $R_{53}$ be a fused ring structure having at least three rings which is selected from those described as preferred examples of $R_{51}$ and $R_{53}$.

Each of the $R_{51}$-$R_{52}$ bond and the $R_{52}$-$R_{53}$ bond may be either a carbon-carbon bond or a carbon-nitrogen bond and is preferably a carbon-nitrogen bond. More preferably, both the $R_{51}$-$R_{52}$ bond and the $R_{52}$-$R_{53}$ bond are a carbon-nitrogen bond.

Specific examples of the compound of formula (V) are shown below.

TABLE 3

| Compound | $R_{51}$ | $R_{52}$ | $R_{53}$ |
|---|---|---|---|
| 101 | | | |
| 102 | | | |
| 103 | | | |
| 104 | | | |

TABLE 3-continued

| Compound | R$_{51}$ | R$_{52}$ | R$_{53}$ |
|---|---|---|---|
| 105 | | | |
| 106 | | | |
| 107 | | | |

TABLE 4

| Compound | R$_{51}$ | R$_{52}$ | R$_{53}$ |
|---|---|---|---|
| 108 | | | |
| 109 | | | |

TABLE 4-continued

| Compound | R$_{51}$ | R$_{52}$ | R$_{53}$ |
| --- | --- | --- | --- |
| 110 | 3,6-di-t-Bu-carbazol-9-yl | 9-phenyl-carbazol-3,6-diyl | 3,6-di-t-Bu-carbazol-9-yl |
| 111 | 3,6-di-Ph-carbazol-9-yl | 9-phenyl-carbazol-3,6-diyl | 3,6-di-Ph-carbazol-9-yl |
| 112 | dibenzo[a,c]carbazol-N-yl | 9-phenyl-carbazol-3,6-diyl | dibenzo[a,c]carbazol-N-yl |
| 113 | 3,6-di-t-Bu-carbazol-9-yl | 9-(anthracen-2-yl)-carbazol-3,6-diyl | 3,6-di-t-Bu-carbazol-9-yl |
| 114 | tribenzo-azepinyl | 9,9-dimethyl-fluoren-2,7-diyl | tribenzo-azepinyl |

TABLE 5

| Compound | R$_{51}$ | R$_{52}$ | R$_{53}$ |
|---|---|---|---|
| 115 | | | |
| 116 | | | |
| 117 | | | |
| 118 | | | |
| 119 | | | |
| 120 | | | |
| 121 | | | |

[Hole Blocking Layer]

The hole blocking layer may be formed of an electron accepting organic material. Examples of the electron accepting organic materials include oxadiazole derivatives, such as 1,3-bis(4-tert-butylphenyl-1,3,4-oxadiazolyl)phenylene (OXD-7), anthraquinodimethane derivatives, diphenylquinone derivatives, bathocuproine (BCP) and its derivatives, bathophenanthroline and its derivatives, triazole compounds, tris(8-hydroxyquinolinato)aluminum (Alq), bis(4-methyl-8-quinolinato)aluminum, distyrylarylene derivatives, and silole compounds. Materials having no electron accepting properties but sufficient electron transport properties may also be used to form the hole blocking layer. Examples of such materials include porphyrin compounds, styryl compounds, such as 4-dicyanomethylene-2-methyl-6(4-(dimethylaminostyryl))-4H pyran (DCM), and 4H pyran compounds.

The thickness of the hole blocking layer is preferably 10 to 200 nm, more preferably 30 to 150 nm, even more preferably 50 to 100 nm. The effect of preventing dark current generation will be sufficiently produced with a thickness of 10 nm or greater, and the reduction in photoelectric conversion efficiency is minimized with a thickness of 200 nm or smaller.

Preferred candidates for the hole blocking materials are Alq and its derivatives, BCP and its derivatives, and the materials described in JP 2007-59515A.

Figure 1B:
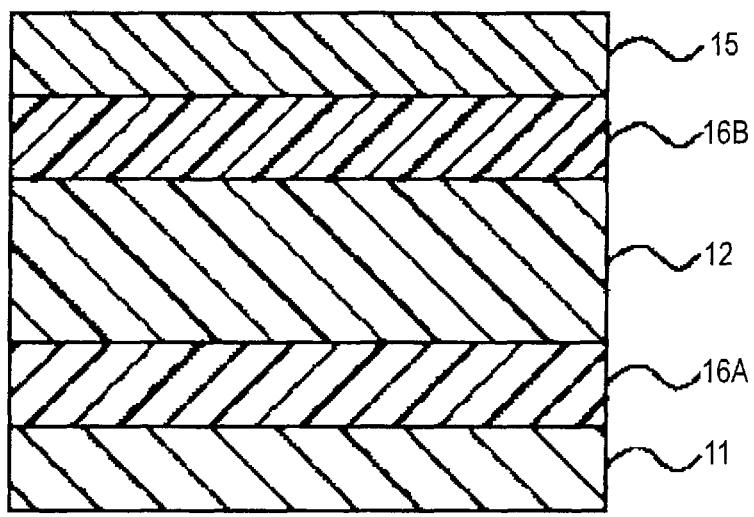

In the cases where the photoelectric element has a hole blocking layer as in the embodiment shown in FIG. 1B, the hole blocking layer is preferably formed of an electron accepting organic material. Examples of the electron accepting organic materials include oxadiazole derivatives, such as 1,3-bis(4-tert-butylphenyl-1,3,4-oxadiazolyl)phenylene (OXD-7), anthraquinodimethane derivatives, diphenylquinone derivatives, bathocuproine (BCP) and its derivatives, bathophenanthroline and its derivatives, triazole compounds, tris(8-hydroxyquinolinato)aluminum (Alq), bis(4-methyl-8-quinolinato)aluminum, distyrylarylene derivatives, and silole compounds. Materials having no electron accepting properties but sufficient electron transport properties may also be used to form the hole blocking layer. Examples of such materials include porphyrin compounds, styryl compounds, such as 4-dicyanomethylene-2-methyl-6(4-(dimethylaminostyryl))-4H pyran (DCM), and 4H pyran compounds. Specifically, the compounds described in JP 2008-72090A are preferably used to make the hole blocking layer.

The electron blocking layer and the hole blocking layer may be formed by vapor deposition, such as PVD or CVD. PVD such as vacuum deposition is preferred to CVD. In the case of vacuum deposition, the degree of vacuum, the deposition temperature, and other deposition conditions may be decided in a usual manner.

In a preferred embodiment, the photoelectric element includes an organic dual layer structure comprising a organic photoelectric layer and an electron blocking layer as hereinafter described with reference to FIG. 1A. In this structure, the electron blocking layer preferably contains a triarylamine, and the photoelectric layer preferably contains the compound of formula (I) and a fullerene or a fullerene derivative. A voltage is preferably applied with the electron blocking layer side as a negative electrode and the photoelectric layer side as a positive electrode. In the case of the embodiment shown in FIG. 1B, too, a voltage is preferably applied with the electron blocking layer side as a negative electrode. The voltage to be applied is selected from the range of from 0 to 100 V, preferably 0 to 40 V, more preferably 0.1 to 20 V. When the photoelectric element of the invention is used as a light sensor or incorporated into an imaging device, a voltage may be applied in the same manner as described.

FIGS. 1A and 1B each illustrate the configuration that the photoelectric element of the invention may take.

The photoelectric element 10a of FIG. 1A has a conductive layer 11 functioning as a lower electrode (hereinafter referred to as a lower electrode 11), an electron blocking layer 16A, an organic photoelectric layer 12, and a transparent conductive layer 15 serving as an upper electrode (hereinafter referred to as an upper electrode 15) stacked in the order named.

The photoelectric element 10b of FIG. 1B has a lower electrode 11, an electron blocking layer 16A, an organic photoelectric layer 12, a hole blocking layer 16B, and an upper electrode 15 stacked in the order described. The stacking order of the electron blocking layer and the photoelectric layer in FIG. 1A and the stacking order of the electron blocking layer, the photoelectric layer, and the hole blocking layer in FIG. 1B may be reversed according to the end use or desired characteristics.

Each of the members constituting the photoelectric element will then be described.

[Electrode]

The electrodes (i.e., the upper transparent electrode 15 and the lower electrode 11) are made of a conductive material, such as a metal, an alloy, a metal oxide, an electrically conductive compound, or a mixture thereof.

Since light falls on the upper electrode 15, the upper electrode 15 must be sufficiently transparent to the light of wavelengths to be detected. Examples of materials forming the transparent upper electrode 15 include conductive metal oxides, such as antimony- or fluorine-doped tin oxide (ATO or FTO), tin oxide, zinc oxide, indium oxide, ITO, and indium zinc oxide (IZO); metals, such as gold, silver, chromium, and nickel; mixtures or laminates of the metal and the conductive metal oxide recited above; inorganic conductive substances, such as copper iodide and copper sulfide; organic conductive substances, such as polyaniline, polythiophene, and polypyrrole; and laminates of ITO with the material recited above. Preferred of them are conductive metal oxides in terms of high conductivity and transparency. Since the upper electrode 15 is formed on the organic photoelectric layer 12, it is preferably formed by a process that does not cause deterioration of the characteristics of the organic photoelectric layer 12.

The lower electrode 11 may be made of either a transparent or reflective material depending on the intended use. Examples of materials forming the lower electrode 15 include conductive metal oxides, such as ATO, FTO, tin oxide, zinc oxide, indium oxide, ITO, and IZO; metals, such as gold, silver, chromium, nickel, titanium, tungsten, and aluminum; conductive metal compounds, including oxides and nitrides of the metals recited, such as titanium nitride (TiN); mixtures or laminates of the metal and the conductive metal oxide recited above; inorganic conductive substances, such as copper iodide and copper sulfide; organic conductive substances, such as polyaniline, polythiophene, and polypyrrole; and laminates of ITO or TiN with the material recited above.

The method of forming the electrodes is not particularly limited and is chosen as appropriate to the electrode material. Available methods include wet processes such as printing and coating, physical processes such as vacuum deposition, sputtering, and ion plating, and chemical processes such as CVD and plasma enhanced CVD.

An ITO electrode may be formed by electron beam (EB) deposition, sputtering, resistance heating deposition, chemical reaction (e.g., sol-gel process), or application of an ITO dispersion. The ITO film thus formed may be subjected to UV-ozone treatment or plasma treatment. A TiN electrode may be formed by various methods such as reactive sputtering. The TiN film thus formed may be subjected to UV-ozone treatment or plasma treatment.

The upper electrode 15 is preferably formed by a plasma-free deposition process so that the adverse influences of a plasma on the substrate may be reduced. As used herein, the term "plasma free" means a state in which a plasma does not generate during deposition or a state in which the substrate is at least 2 cm, preferably 10 cm or more, more preferably 20 cm or more, distant from the source of plasma generation so that the plasma is reduced before it reaches the substrate.

A plasma free deposition system involving no plasma generation during deposition is exemplified by an EB deposition system and a pulse laser deposition system. Examples of an EB deposition system and a pulse laser deposition system are described in *TOMEI DODENMAKU NO SHINTENKAI*, supervised by Yutaka Sawada, CMC Publishing, 1999; *TOMEI DODENMAKU NO SHINTENKAI II*, supervised by Yutaka Sawada, CMC Publishing, 2002; *TOMEI DODENMAKU NO GIJUTSU*, Japan Society for the Promotion of Science, Ohmsha, Ltd., 1999; and references cited therein.

A film formation system (layer-fabrication system) in which the distance between a plasma source and a substrate is 2 cm or longer so that plasma is lessened before it reaches the substrate (hereinafter referred to as a plasma-free deposition system) may be exemplified by a facing target sputtering system and an arc plasma deposition system. Examples of suitable plasma free deposition systems are described in *TOMEI DODENMAKU NO SHINTENKAI*, supervised by Yutaka Sawada, CMC Publishing, 1999; *TOMEI DODENMAKU NO SHINTENKAI II*, supervised by Yutaka Sawada, CMC Publishing, 2002; *TOMEI DODENMAKU NO GIJUTSU*, Japan Society for the Promotion of Science, Ohmsha, Ltd., 1999; and references cited therein.

When the upper electrode 15 is a transparent conductive layer of, e.g., a transparent conductive oxide, (TCO), a DC short circuit or an increase in leak current can occur. One of the causes thereof is considered to be as follows. Fine cracks introduced into the organic photoelectric layer 12 are filled with a dense film of, e.g., a TCO, which can result in an increase of electrical continuity to the opposite lower electrode 11. In the case where the upper electrode 15 is made of a material providing relatively poor film properties, such as aluminum, an increase in leak current is not likely to occur. Such an increase in leak current can greatly be prevented by controlling the thickness of the upper electrode 15 with respect to the thickness of the organic photoelectric layer 12, i.e., the depth of cracks. From this viewpoint, the thickness of the upper electrode 15 is preferably ⅕ or less, more preferably ¹⁄₁₀ or less, of that of the organic photoelectric layer 12.

In general, reducing the thickness of a conductive layer below a certain limit results in an abrupt increase of resistance. Because the sheet resistance of the solid state imaging device having the photoelectric element of the invention is preferably 100 to 10,000 Ω/sq., there is a great freedom to reduce the thickness of the conductive layer. Furthermore, the smaller the thickness of the upper electrode (transparent conductive layer) 15, the less the light is absorbed thereby, which generally leads to an increase in light transmittance. An increase in light transmittance of the transparent upper electrode brings about an increase in light absorption by the organic photoelectric layer and a resultant increase in photoelectric conversion performance. Considering that reduction in thickness of the upper electrode 15 leads to reduction in increase of leak current, increase in resistivity of the upper electrode, and increase in transmittance of the upper electrode, the thickness of the upper electrode is preferably 5 to 100 nm, more preferably 5 to 20 nm.

[Light Sensor]

Photoelectric elements are roughly divided into light sensors and photocells. The photoelectric element of the invention is suitable as a light sensor. The light sensor may have a single photoelectric element or a plurality of photoelectric elements arrayed one-dimensionally (a line sensor) or two-dimensionally (a two-dimensional sensor). The line sensor converts optical image information to electric signals using an optical system and a driving part like a scanner to perform the function as an imaging device. The two-dimensional sensor forms an image of optical image information on a sensor and converts the image to electric signals to perform the imaging function.

A photocell is a power-generating unit. While the light to electrical energy conversion efficiency is an importance factor for a photocell, dark current which is a flow of electricity produced in the absence of light poses no functional problem. Furthermore, fabrication of a photocell does not include a heating step as involved in the production of a light sensor, such as the step of providing a color filter. On the other hand, it is an important performance criterion for a light sensor to convert bright and dark signals to electric signals at high accuracy. Not only a high light to electric current conversion efficiency but also a low dark current are required because a signal outputted in the absence of light causes noise. Resistance to the post treatments such as heating is also of importance.

[Driving Method]

The invention also relates to a method of driving a photoelectric element. That is, the invention provides a method of driving the photoelectric element of the invention or the photoelectric element used in the imaging device of the invention. The photoelectric element is preferably driven by applying an electric field of $1 \times 10^{-4}$ V/cm to $1 \times 10^{7}$ V/cm between the conductive layer and the transparent conductive layer serving as a pair of electrodes. To ensure reduction of dark current, it is preferred that the electric field be applied with one of the electrodes that is in contact with the electron blocking layer serving as a negative electrode and with the other as a positive electrode. To obtain higher sensitivity and lower dark current, the electric field intensity to be applied between the electrodes is preferably $1 \times 10^{2}$ to $2 \times 10^{6}$ V/cm, more preferably $1 \times 10^{4}$ to $1 \times 10^{6}$ V/cm.

In terms of light utilization and heat resistance of the element, it is preferred that light be allowed to impinge on the side of the electrode not being in contact with the electron blocking layer.

[Imaging Device]

The structure of the imaging device having a photoelectric element 10a will be illustrated with reference to FIG. 2. In the following description, parts or members equivalent in configuration or function to those previously described will be identified by the same or equivalent numerals in the drawings and will not be redundantly described.

An imaging device is a device that converts optical image information to electric signals, in which a plurality of photoelectric elements are arrayed coplanarly on a matrix. Each photoelectric element called a pixel converts a light signal to an electric signal and outputs the electric signal out of the imaging device. Each pixel includes one photoelectric element and one or more transistors.

Figure 2:
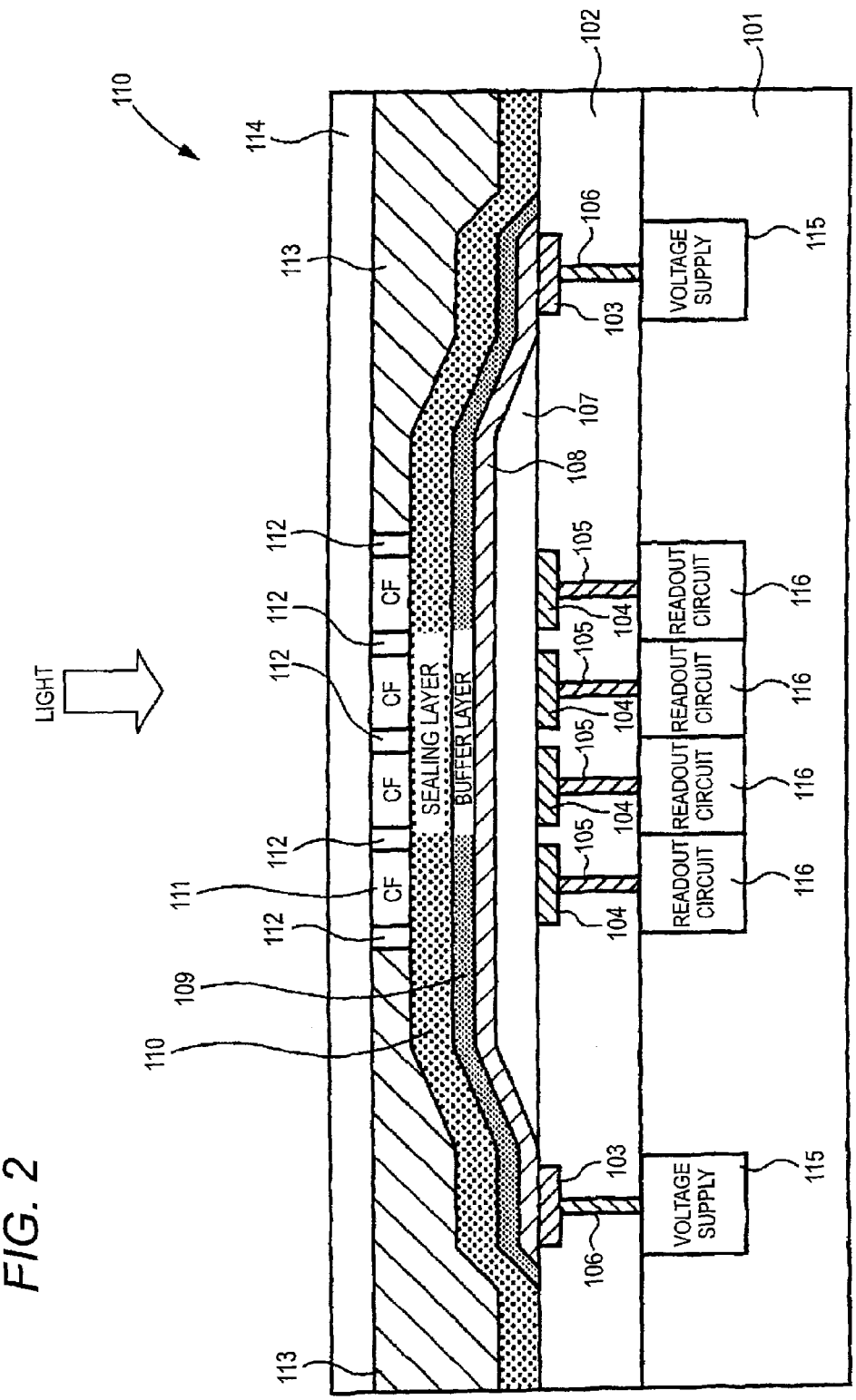
FIG. 2 is a schematic cross-section illustrating an imaging device incorporating an embodiment of the invention.

FIG. 2 is a schematic cross-section showing the structure of an imaging device 100 incorporating an exemplary embodiment of the invention. The imaging device of this embodiment is used to be mounted on an imaging apparatus, such as a digital still camera or a digital video camera, or an imaging module of an endoscope, a mobile phone, and the like. The imaging device 100 has a plurality of photoelectric elements having such a layer structure as illustrated in FIG. 1 coplanarly either one dimensionally or two dimensionally on a circuit board having readout circuits that read the signal corresponding to the charge photogenerated in the photoelectric layer of the respective photoelectric elements.

The imaging device 100 of FIG. 2 includes a substrate 101, an insulating layer 102, connection electrodes 103, pixel electrodes (or lower electrodes) 104, vertical interconnects 105 and 106, an organic layer 107 which includes a photoelectric layer and a blocking layer, a counter electrode (or upper electrode) 108, a buffer layer 109, a sealing layer 110, color filters (CF) 111, partition walls 112, a light-shielding layer 113, a protective layer 114, a voltage supply 115 for supplying voltage to the counter electrode, and readout circuits 116.

Each pixel electrode 104 has the same function as the electrode 11 of the photoelectric element 10a shown in FIG. 1. The counter electrode 108 has the same function as the electrode 15 of the photoelectric element 10a of FIG. 1. The organic layer 107 has the same structure as the layer provided between the electrodes 11 and 15 in FIG. 1.

The substrate 101 is a glass substrate or a semiconductor (e.g., Si) substrate. The insulating layer 102 is formed on the substrate 101. A plurality of pixel electrodes 104 and a plurality of connection electrodes 103 are formed in the surface portion of the insulating layer 102.

The organic layer 107 is formed on the pixel electrodes 104 to cover them and to be shared by all the photoelectric elements.

The counter electrode 108 is disposed on the organic layer 107 to be commonly shared by all the photoelectric elements. The counter electrode 108 extends to cover the connection electrodes 103 disposed outside the organic layer 107 and is electrically connected to the connection electrodes 103.

The vertical interconnect 106, such as a via plug, is buried in the insulating layer 102 to connect the connection electrode 103 and the voltage supply 115. The voltage supply 115 is formed in the substrate 101 and applies a prescribed voltage to the counter electrode 108 via the interconnect 106 and the connection electrode 103. In the case when the voltage supplied to the counter electrode 108 is higher than the power source voltage of the imaging device, the power source voltage is raised to the prescribed voltage through a voltage booster, such as a charge pump.

The readout circuits 116 are formed in the substrate 101 in correspondence with the respective pixel electrodes 104 and read out signals in response to the charges collected in the respective pixel electrodes 104. Each readout circuit 116 is composed of a CCD circuit, a CMOS circuit, a TFT circuit, and so on. The readout circuits 116 are shielded from light by an unshown light-shielding layer provided in the insulating layer 102. The readout circuits 116 are electrically connected to the respective pixel electrodes 104 via the respective interconnects 105.

The buffer layer 109 is provided on the counter electrode 108 to cover the counter electrode 108. The sealing layer 110 is provided on the buffer layer 109 to cover the buffer layer 109. The color filters 111 are disposed on the sealing layer 110 at positions corresponding to the respective pixel electrodes 104. The partition walls 112 are disposed between the color filters 111 to ensure light transmission efficiency of the color filers 111.

The light shielding layer 113 is provided on the sealing layer 110 in the area other than the regions having the color filters 111 and the partition walls 112 to prevent light from entering the organic layer 107 in the area other the effective pixel area. The protective layer 114 is provided on the color filters 111, the partition walls 112, and the light-shielding layer 113 to protect the whole imaging device 100.

When light impinges on the imaging device 100 having the configuration described, it enters the photoelectric layer 100 to generate charges (hole-electron pair). The holes are collected by the pixel electrodes 104, and the voltage signals corresponding to the amount of the holes are outputted from the imaging device 100 by the readout circuits 116.

The imaging device 100 is fabricated as follows. On a circuit board having formed therein voltage supplies 115 and readout circuits 116 are formed vertical interconnects 105 and 106, connection electrodes 103, pixel electrodes 104, and an insulating layer 102. The pixel electrodes 104 are arranged in the surface portion of the insulating layer 102 in, for example, a square grid pattern.

A organic layer 107 is then deposited on the pixel electrodes 104 by, for example, vacuum evaporation. A counter electrode 108 is deposited on the organic layer 107 by, for example, sputtering in vacuo. On the counter electrode 108 are sequentially deposited a buffer layer 109 and a sealing layer 110 by, for example, vacuum evaporation. Color filters 111, partition walls 112, and a light shielding layer 113 are then formed. Finally, a protective layer 114 is formed to complete the imaging device 100.

In the fabrication of the imaging device 100, incorporating a step wherein a precursor of the imaging device 100 is placed under non-vacuum conditions between the step of forming the photoelectric layer included in the organic layer 107 and the step of forming the sealing layer 110 will not interfere with the prevention of performance deterioration of the photoelectric elements. Incorporating such a step is effective in reducing the fabrication cost while preventing the performance deterioration of the imaging device 100.

The details of the sealing layer 110, one of the members constituting the imaging device 100 are hereinafter described.

[Sealing Layer]

The sealing layer 110 is required to satisfy the following conditions.

(1) To protect the photoelectric layer, the sealing layer 110 should inhibit penetration of organic photoelectric material-deteriorating factors contained in a solution, a plasma, etc. used in the imaging device fabrication.

(2) To prevent deterioration of the photoelectric layer included in the organic layer 107 during long time storage and use, the sealing layer 110 should inhibit penetration of organic photoelectric material-deteriorating factors, such as water molecules, after the imaging device fabrication.

(3) The sealing layer 110 should be such that may be formed under conditions that do not deteriorate the photoelectric layer already formed.

(4) To let incident light reach the photoelectric layer included in the organic layer 107 via the sealing layer 110, the sealing layer 110 must be transparent to the light rays having wavelengths detectable by the photoelectric layer.

The sealing layer 110 may have a single layer structure of a single material or a multilayer structure composed of sealing sublayers performing the respective functions. A multilayer structure is expected to provide advantages such that the stress of the whole sealing layer 110 is relaxed; occurrence of defects caused by dust during the fabrication, such as a crack and a pinhole, is minimized; and optimum material design is provided. For instance, the sealing layer 110 may have a dual layer structure having a first sealing sublayer that performs the essential function of inhibiting penetration of deteriorating factors, such as water molecules, and a second sealing sublayer (an auxiliary sealing sublayer) provided on the first sealing sublayer, the second sealing sublayer being designed to perform any function that is difficult to achieve by the first sealing sublayer. The number of the sublayers may be three or even more but is limited by considerations of cost.

An organic photoelectric material deteriorates considerably in the presence of a deteriorating factor, such as water molecules. It is therefore necessary to cover and seal the whole photoelectric layer with a water-impermeable dense material, such as ceramics including metal oxides, metal nitrides, and metal oxynitrides, and diamond-like-carbon. It is a generally followed practice to form a sealing layer of aluminum oxide, silicon oxide, silicon nitride, silicon oxynitride, or a stack thereof, or a laminate of such a ceramic layer and an organic polymer by various vacuum deposition techniques. According to these conventional film formation processes ( ), however, a step (level difference) on the substrate due to, for example, a structure of the substrate surface, a micro defect on the substrate surface, or a particle attached to the substrate surface blocks deposition and makes film growth difficult. As a result, the film deposited over the step is remarkably thinner than a flat area of the film and can provide a channel for allowing the deteriorating factor to penetrate. In order to completely cover the step with a sealing layer, it is necessary to form the sealing layer with such a large thickness that the thickness on the flat area may be at least 1 μm.

In the case of an imaging device having a pixel size of less than 2 μm, particularly about 1 μm, if the distance between a color filter 111 and the photoelectric layer, namely the thickness of the sealing layer is large, incident light can diffract and/or diffuse in the sealing layer 110, resulting in color cross-talk or color mixing. It is therefore necessary, with an imaging device having a pixel size of about 1 μm, that a material and method for forming a sealing layer be selected so that the device performance may not deteriorate even with the thickness of the sealing layer reduced.

Atomic layer deposition (ALD), one of CVD processes, is a thin film formation technique consisting of alternately repeating adsorption and reaction of an organometallic compound molecules, metal halide molecules, or metal hydride molecules to and on the surface of a substrate and decomposition of any unreacted group of the reaction product. Since the film-forming material is a low molecular compound when it reaches the substrate, the deposit is able to grow only if there is a space in which small molecules are allowed to diffuse. Thus, the step on the substrate surface, which is due to a structure of the substrate surface, a micro defect on the substrate surface, or a particle attached to the substrate surface, is completely covered to form a deposit equally thick on both the step and the flat area. In short, ALD demonstrates excellent step coverage and prevents the step from providing a penetration path for the photoelectric material-deteriorating factor. ALD allows for reducing the effective thickness of the sealing layer 110 compared with the thickness of the sealing layer formed by other conventional film formation techniques.

When the sealing layer 110 is formed by ALD, the precursor materials to be used in ALD are appropriately selected from those providing the ceramics described supra. Nevertheless, since the photoelectric layer to be sealed contains an organic photoelectric material, the ALD precursor materials are limited to those capable of growing into film at relatively low temperatures so as to avoid thermal deterioration of the organic photoelectric material. ALD using an alkylaluminum or an aluminum halide as a precursor provides a capability of growing a dense aluminum oxide film (layer) at temperatures lower than 200° C. that does not cause deterioration of the underlying organic photoelectric material. ALD using trimethylaluminum is particularly preferred; for it provides a capability of growing an aluminum oxide film (layer) at around 100° C. Similarly to an aluminum oxide film, a dense film of silicon oxide or titanium oxide may also be formed by ALD at temperatures lower than 200° C. by proper selection of the precursor material.

EXAMPLES

The invention will now be illustrated in greater detail with reference to Synthesis Examples and Examples, but it should be understood that the invention is not deemed to be limited thereto. As will be appreciated by those skilled in the art, the presence of a substituent on the compound defined above has little influence on the effects of the invention so that the effects achieved in the following Examples will be obtained if in using the corresponding compounds having any substituent.

Synthesis Example 1

Synthesis of Compound 1

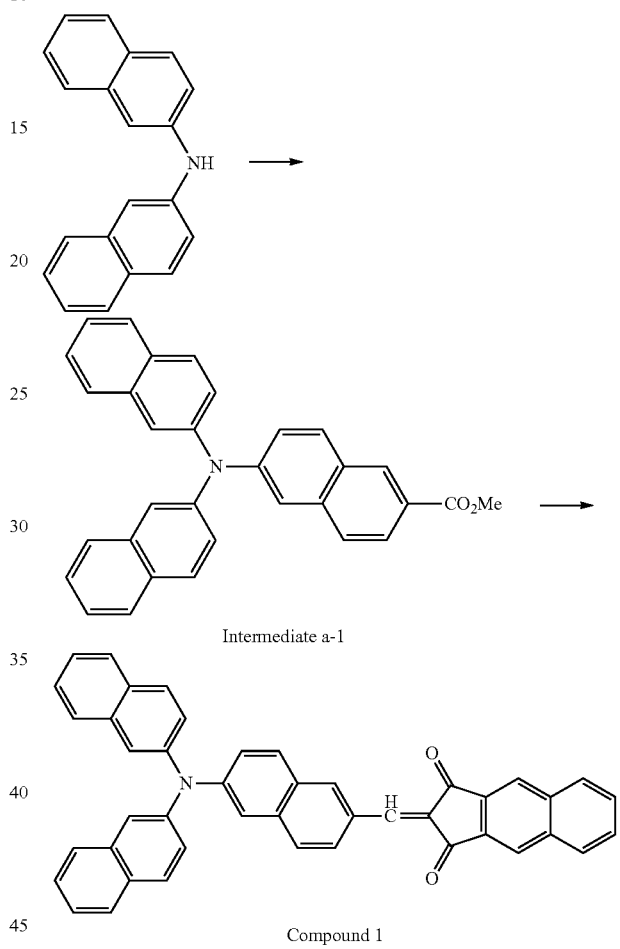

To 10 ml of dry xylene were added 4.4 g of di(2-naphthyl) amine (from Tokyo Chemical Industry), 4 g of methyl 6-bromo-2-naphthoate (from Wako Pure Chemical), 0.2 g of palladium acetate, 0.6 g of triphenylphosphine, and 10 g of cesium carbonate, and the mixture was refluxed for 6 hours in a nitrogen stream. The reaction mixture was filtered by suction, and the filtrate was concentrated and purified by column chromatography on silica gel using toluene as a developing solvent. Removal of the solvent by evaporation gave 6 g of intermediate a-1.

To 30 ml of dry toluene was added 24 ml of a toluene solution (about 70%) of sodium bis(2-methoxyethoxy)aluminum hydride (SMEAH) (from Wako Pure Chemical). After cooling to 0° C. in an ice bath, a solution of 10 ml of 1-methylpiperazine in 17 ml of dry toluene was added thereto dropwise. Separately, 6 g of intermediate a-1 was dissolved in 50 ml of dry toluene, and the solution was cooled to −40° C. in a dry ice bath, and the SMEAH solution prepared above was added thereto dropwise. The mixture was stirred for 5 hours in a nitrogen stream. The reaction mixture was adjusted to pH 1 with concentrated hydrochloric acid, and water and ethyl acetate were added thereto. The oil layer was washed with an aqueous solution of sodium hydrogencarbonate, dried over magnesium sulfate, and filtered. The solvent was removed by evaporation. To one-third of the residue were added 1.3 g of benz[f]indane-1,3-dione synthesized in accordance with *J. Med. Chem.*, vol. 16, pp. 1334-1339, 1973 and 100 ml of ethanol, followed by refluxing for 6 hours in a nitrogen stream. The reaction system was allowed to cool and filtered by suction. The filter cake was dissolved in a small amount of chloroform and crystallized from ethanol. The crystals were collected by filtration with suction and dried in vacuo to yield 2 g of compound 1. Compound 1 had a melting temperature of 309° C. as measured using a thermogravimetry/differential thermal analyzer (TG/DTA 6200 AST-2 from SII Nanotechnology). The absorption spectrum of compound 1 in a dilute chloroform solution showed an absorption peak at 548 nm. The molar extinction coefficient at that wavelength was 54,000 $M^{-1}cm^{-1}$. The resulting compound 1 was deposited by vacuum evaporation on a glass substrate to a thickness of 100 nm. The deposited film (layer) had an IP of 5.4 eV as measured with AC-2 from Riken Keiki. As a result of observing the film form under a scanning electron microscope (SEM), the film was smooth and confirmed to be amorphous.

Synthesis Example 2

Synthesis of Compound 2

Compound 2 was synthesized in the same manner as for compound 1, except for replacing di(2-naphthyl)amine with N-(2-anthryl)-2-naphthylamine prepared in accordance with *J. Chem. Soc.*, pp 4308-4310, 1958. The melting temperature of compound (A-2) was 313° C. The absorption spectrum of compound 2 in a dilute chloroform solution showed an absorption peak at 553 nm. The molar extinction coefficient at that wavelength was 50000 $M^{-1}cm^{-1}$. A vacuum deposited film (layer) of compound 2 had an IP of 5.4 eV. As a result of the SEM analysis, the film was smooth and confirmed to be amorphous.

Synthesis Example 3

Synthesis of Compound B

To 20 ml of ethanol were added 2.7 g of 4-(diphenylamino)benzaldehyde and 1.5 g of 1,3-indanedione, and the mixture was heated under reflux for 6 hours in a nitrogen atmosphere, followed by cooling to room temperature. The crystals thus formed were collected by filtration and dissolved in chloroform. Addition of ethanol resulted in recrystallization. The crystals were collected by filtration and washed with ethanol to give 3 g of compound B having a melting temperature of 257° C. The absorption spectrum of compound (B-1) in a dilute chloroform solution showed an absorption peak at 449 nm. The molar extinction coefficient at that wavelength was 54000 $M^{-1}cm^{-1}$. A film (layer) formed of compound (B-1) by vacuum evaporation deposition had an IP of 5.4 eV. As a result of the SEM analysis, the film was smooth and confirmed to be amorphous.

Synthesis Example 4

Synthesis of Compound 31

Compound 31 was synthesized in the same manner as for compound 1, except for replacing di(2-naphthyl)amine with 2-phenylaminonaphthalene (from Tokyo Chemical Industry) and replacing methyl 6-bromonaphthoate with methyl 6-bromobenzoate (from Wako Pure Chemical). The melting temperature of compound 3 was 236° C. The absorption spectrum of compound 31 in a dilute chloroform solution showed an absorption peak at 524 nm. The molar extinction coefficient at that wavelength was 64000 $M^{-1}cm^{-1}$. A film (layer) formed of compound 31 by vacuum evaporation deposition had an IP of 5.5 eV. As a result of the SEM analysis, the film was smooth and confirmed to be amorphous.

Synthesis Example 5

Synthesis of Compound 32

Compound 32 was synthesized in the same manner as for compound 31, except for replacing 2-phenylaminonaphthalene with di(p-tolyl)amine (from Tokyo Chemical Industry). The melting temperature of compound 32 was 278° C. The absorption spectrum of compound 32 in a dilute chloroform solution showed an absorption peak at 529 nm. The molar extinction coefficient at that wavelength was 63000 $M^{-1}cm^{-}$1. A film (layer) formed of compound 32 by vacuum evaporation deposition had an IP of 5.4 eV. As a result of the SEM analysis, the film was smooth and confirmed to be amorphous.

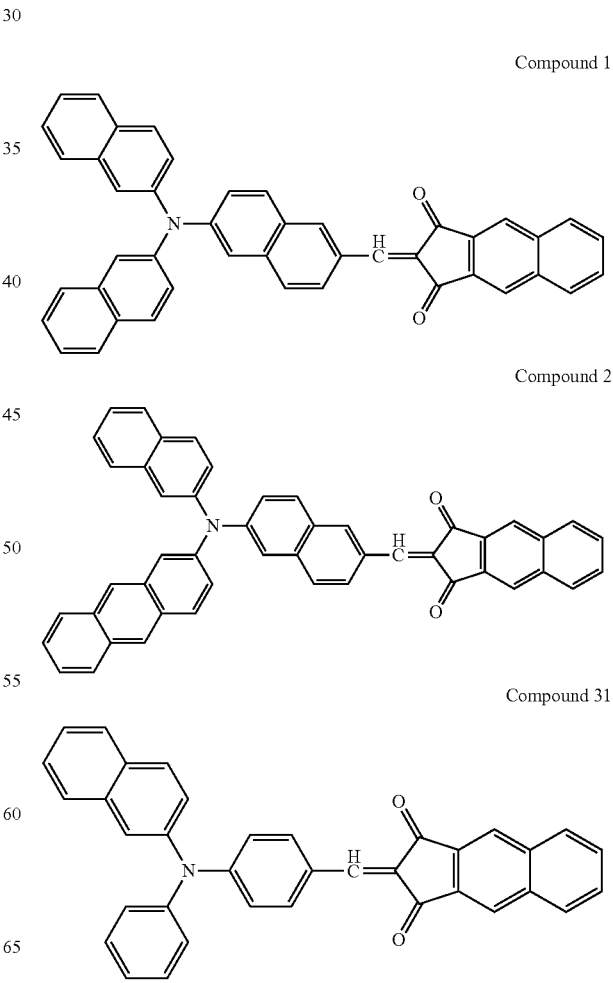

Compound 1

Compound 2

Compound 31

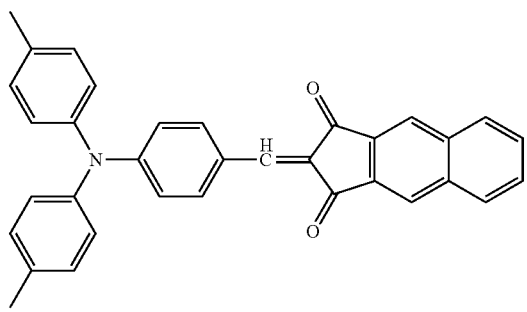

Compound 32

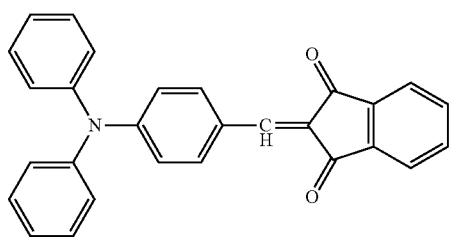

Compound B

[Preparation of Electron Blocking Material]

The compounds shown below for use as an electron blocking material were synthesized in accordance with literature procedures as described below. Where needed, the resulting compound was purified by sublimation or distillation using TRS-160 from Ulvac-Riko at a degree of vacuum of 0.07 Pa. The IP of a deposited film (layer) of each compound is shown under the name of the compound.

"Spiro-1-NBP" was synthesized by the reaction between tetrabromospirobifluorene and 1-phenylaminonaphthalene in toluene in the presence of anhydrous potassium carbonate, palladium acetate, and tri(t-butyl)phosphine. "TPT-1" was synthesized by allowing 4,4'-dibromobiphenyl and 4-diphenylamino-4'-phenylaminobiphenyl to react with each other in the same manner as for spiro-1-NBP. "TBFABT" was prepared by the reaction between 1,3,5-tris(4-bromophenyl)benzene and bis(9,9'-dimethylfluoren-2-yl)amine in the same manner as for spiro-1-NBP. "TFLFL" was prepared by the reaction between 2,7-dibromofluorene and bis(9,9'-dimethylfluoren-2-yl)amine in the same manner as for spiro-1-NBP. "TFLCz" was prepared by the reaction between N-(3-methylphenyl)-3,6-dibromocarbazole and bis(9,9'-dimethylfluoren-2-yl)amine in the same manner as for spiro-1-NBP. "BBCPC" was prepared by the reaction between N-phenyl-2,7-dibromocarbazole and 3,5-di(t-butyl)carbazole in the same manner as for Spiro-1-NBP. "BBCAC" was prepared by the reaction between N-(2-anthryl)-2,7-dibromocarbazole and 3,5-di(t-butyl)carbazole in the same manner as for Spiro-1-NBP. "BTBAF" was prepared by the reaction between 2,7-dibromofluorene and tribenzoazepine in the same manner as for spiro-1-NBP.

"BCBF" was synthesized by the reaction between 7,7'-dibromo-2,2'-bis(9,9'-dimethylfluorene) (synthesized with reference to Tetrahedron Letters, vol. 48, No. 1, pp. 89-93, 2007) and 3,6-di(t-butyl)-9H-carbazole (synthesized by a known process) in toluene in the presence of anhydrous potassium carbonate, palladium acetate, and tri(t-butyl)phosphine. "BABF" was prepared in the same manner as for BCBF, except for replacing 3,6-di(t-butyl)-9H-carbazole with 9,9-dimethyl-9,10-dihydroacridine synthesized in accordance with procedures described in Chemische Berichte, vol. 113, No. 1, p. 358, 1980.

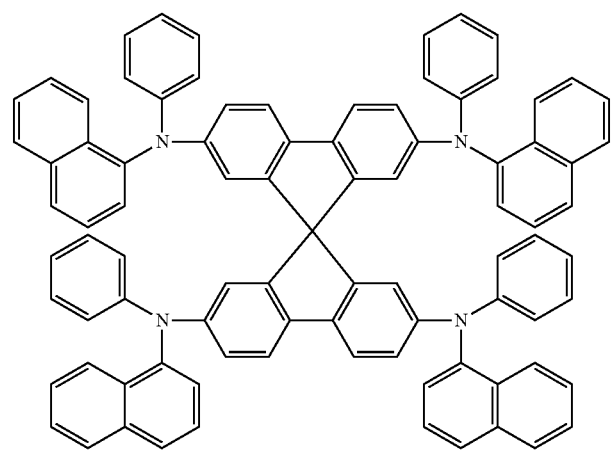

spiro-1-NPB
IP 5.3 eV

-continued
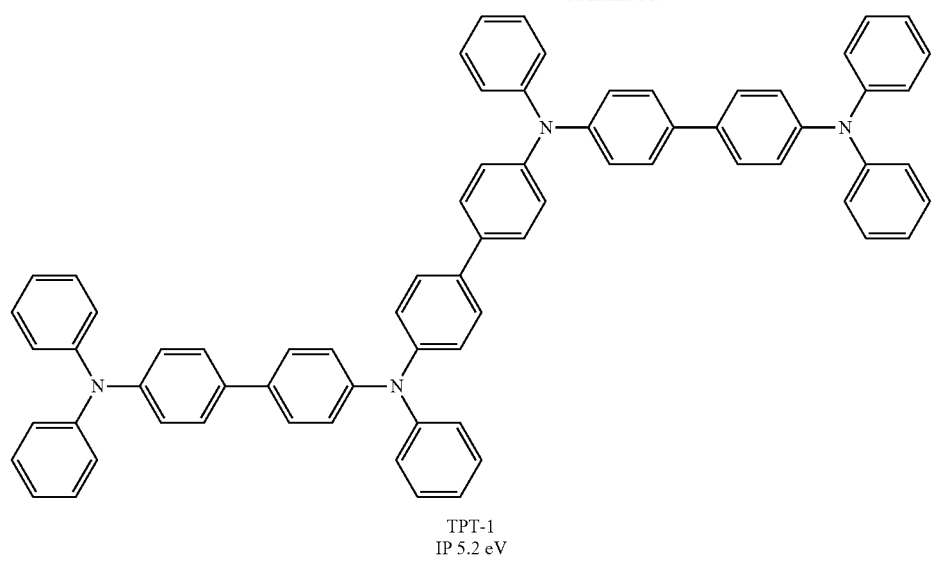
TPT-1
IP 5.2 eV
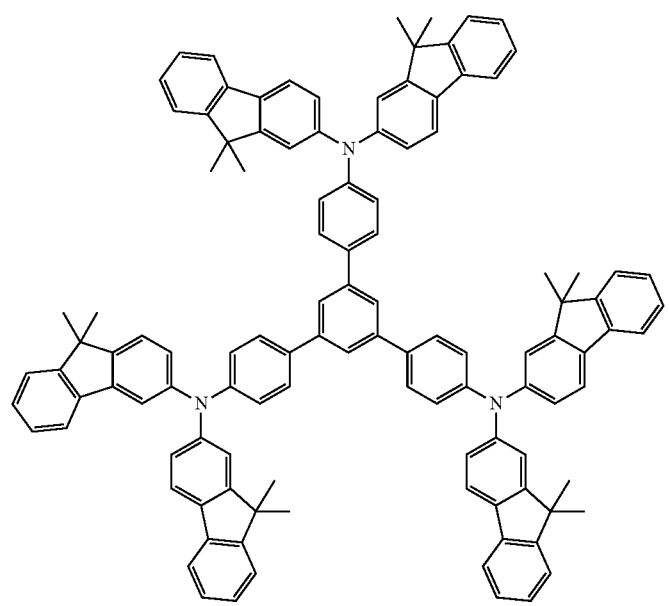
TBFABT
IP 5.3 eV

-continued
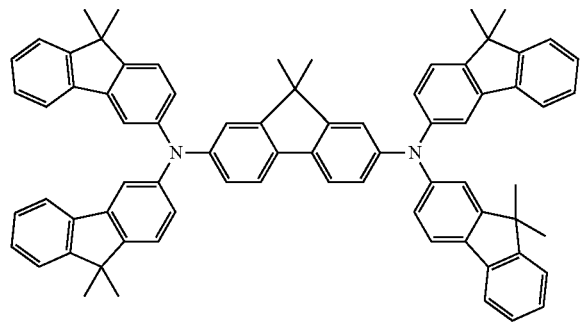
TFLFL
IP 5.0 eV
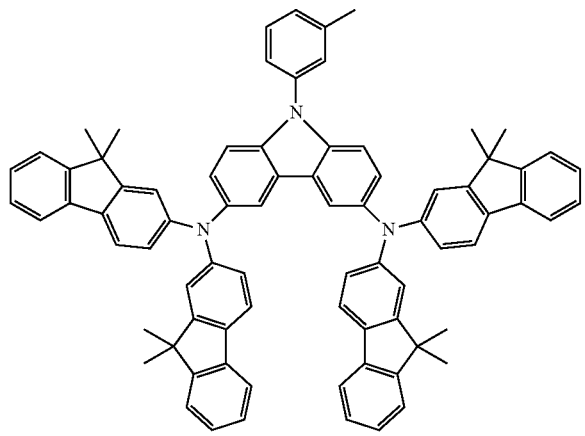
(Compound 107)
TFLCz
IP 5.2 eV
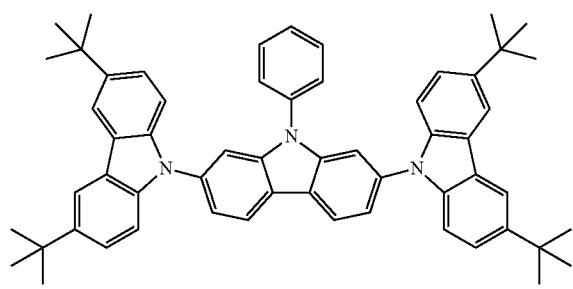
(Compound 110)
BBCPC
IP 5.5 eV
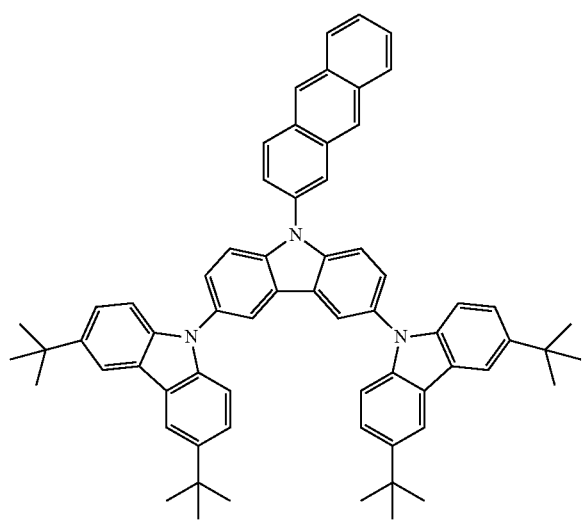
(Compound 113)
BBCAC
IP 5.5 eV
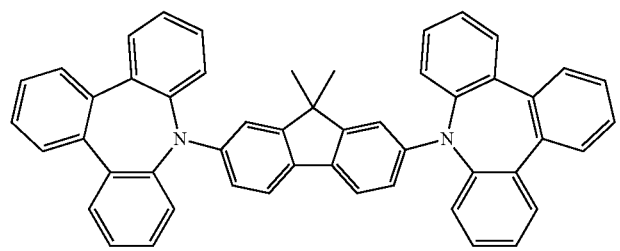
(Compound 114)
BTBAF
IP 5.0 eV (Compound 119)

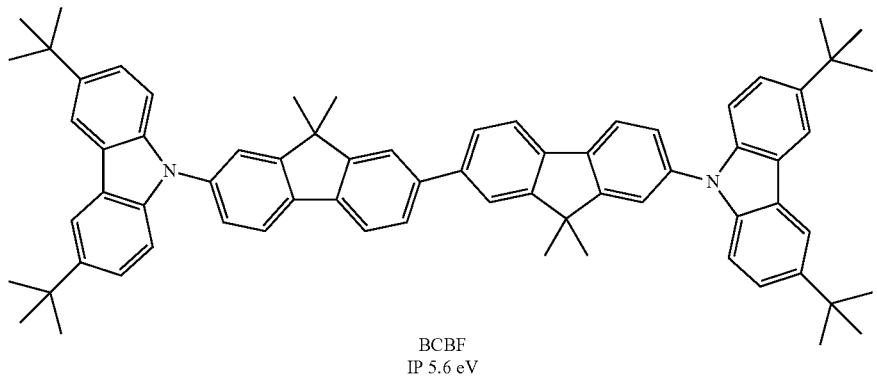

BCBF
IP 5.6 eV (Compound 120)

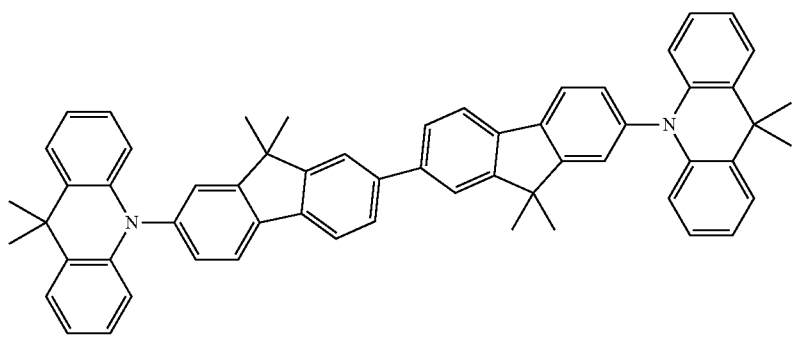

BABF
IP 5.6 eV

The absorption spectrum of these compounds in a dilute chloroform solution showed an absorption peak at 379 nm as for spiro-1-NBP; 342 nm as for TPT-1; 373 nm as for TBFABT; 367 nm as for TFLFL; 353 nm as for TFLCz; 349 nm as for BBCPC; 349 nm as for BBCAC; 356 nm as for BTBAF; 355 nm as for BCBF; and 350 nm as for BABF.

The following commercially available compounds were used as an electron blocking material after purification by sublimation in the same manner as described above.

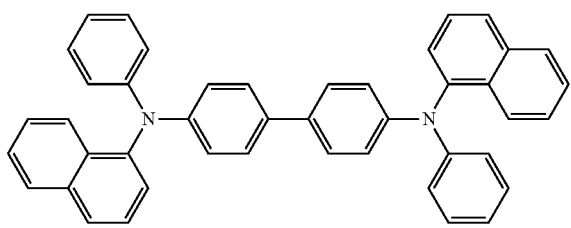

α-NPD
IP 5.5eV

-continued

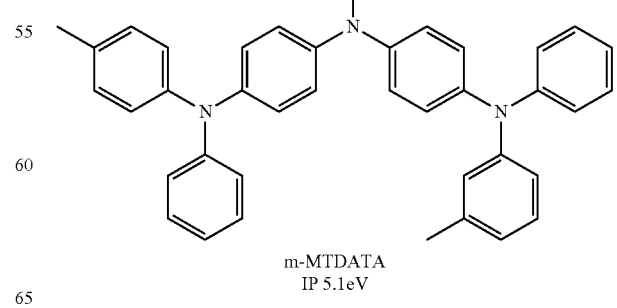

m-MTDATA
IP 5.1eV

Example 1

An element having the structure shown in FIG. 1A was fabricated as follows. Amorphous ITO was deposited on a glass substrate by sputtering to a thickness of 30 nm to form a lower electrode. Spiro-1-NBP was deposited thereon to a thickness of 60 nm by vacuum evaporation to form an electron blocking layer. Compound 1 as a p type photoelectric material and fullerene ($C_{60}$) were co-deposited at a ratio of 1:4 by vacuum evaporation to form a 400 nm thick mixed photoelectric layer. The vacuum evaporation deposition of the photoelectric layer was conducted at a degree of vacuum of $4 \times 10^{-4}$ Pa or less and at a substrate temperature controlled at 25° C. Amorphous ITO was deposited on the photoelectric layer by sputtering to a thickness of 10 nm to form a transparent conductive layer (upper electrode). The resulting stack was sealed in a glass tube to make an imaging device having a photoelectric element.

Examples 2 to 13 and Comparative Examples 1 to 4

Imaging devices were made in the same manner as in Example 1, except for changing the electron blocking material and the p type photoelectric material as shown in Table 6 below.

[Evaluation]

Each of the resulting imaging devices was inspected as follows to see if the photoelectric element thereof functions. A driving voltage to be applied between the upper and the lower electrode was decided so that the dark current of the element of Comparative Example 1 might be 1 nA/cm². Such a driving voltage was about 10 V, which corresponded to an electric field intensity of $2 \times 10^5$ V/cm. The voltage was applied with the lower electrode, which was in contact with the electron blocking layer, as a negative electrode and the upper electrode as a positive electrode. Every device was driven in that way, and a dark current was determined at room temperature. The imaging device was then irradiated on its upper electrode side (the side of the electrode that was not in contact with the electron blocking layer) with a given amount of light with the voltage applied to determine an external quantum efficiency (EQE). As a result, every device had a dark current of $1 \times 10^{-9}$ A/cm² or less, which is a sufficiently low value, and an EQE of 50% or more, which is sufficiently high.

Each device was maintained on a hot plate at 180° C. for 30 minutes. After allowing the device to cool to room temperature, a dark current and an EQE were determined and expressed relatively with respect to those determined before heating. The results obtained are shown in Table 6.

TABLE 6

|  | P Type Photoelectric Material | | Electron Blocking Material | | EQE after Heating (relative to the value before heating) | Dark Current after Heating (relative to the value before heating) |
| --- | --- | --- | --- | --- | --- | --- |
|  | Compound | Tg (° C.) | Compound | Tg (° C.) | | |
| Example 1 | 1 | 146 | spiro-1-NBP | 146 | 0.94 | 5.1 |
| Example 2 | 2 | 151 | spiro-1-NBP | 146 | 0.96 | 6 |
| Example 3 | 1 | 146 | TPT-1 | 143 | 0.95 | 4.1 |
| Example 4 | 1 | 146 | BTBAF | 174 | 0.98 | 1.4 |
| Example 5 | 1 | 146 | TBFABT | 189 | 0.99 | 1.3 |
| Example 6 | 1 | 146 | TFLFL | 186 | 1.01 | 1.4 |
| Example 7 | 1 | 146 | TFLCz | 191 | 1 | 1.2 |
| Example 8 | 1 | 146 | BABF | 210 | 0.99 | 0.95 |
| Example 9 | 1 | 146 | BBCPC | 217 | 1.01 | 0.9 |
| Example 10 | 1 | 146 | BBCAC | 228 | 0.99 | 0.8 |
| Example 11 | 1 | 146 | BCBF | 245 | 1 | 0.75 |
| Example 12 | 31 | 105 | spiro-1-NBP | 146 | 0.92 | 17 |
| Example 13 | 32 | 103 | spiro-1-NBP | 146 | 0.9 | 23 |
| Compara. Example 1 | B | 88 | α-NPD | 97 | 0.69 | >1000 |
| Compara. Example 2 | B | 88 | m-MTDATA | 75 | 0.7 | >1000 |
| Compara. Example 3 | 1 | 146 | m-MTDATA | 75 | 0.78 | >500 |
| Compara. Example 4 | B | 88 | spiro-1-NBP | 146 | 0.72 | >100 |

In Comparative Examples 1 to 4, the device undergoes great reduction in EQE and extremely large increase in dark current as a result of heating. In contrast, both the reduction in EQE and the increase in dark current caused by heating are smaller in Examples 1 through 13 than in Comparative Examples 1 to 4, proving the devices of Examples to have high heat resistance. In particular, the devices of Examples 4 to 11 show practically no change in EQE and a small increase in dark current. It is noteworthy that the devices of Examples 8 to 11 using a p type organic photoelectric material with a Tg of 140° C. or higher and an electron blocking material with a Tg of 200° C. or higher show reduction in dark current on being heated, surprisingly revealing that the device performance improves rather than deteriorates as a result of heating.

Additionally, an imaging device having the structure shown in FIG. 2 was fabricated as follows. Amorphous ITO was sputtered on a CMOS substrate to a thickness of 30 nm. The deposited ITO layer was photolithographically patterned into lower electrodes such that there might be one pixel on each photodiode of the CMOS substrate. An electron blocking layer, a photoelectric layer, and an upper electrode were stacked thereon in the same manner as in Example 1. The resulting imaging device was evaluated in the same manner as in Example 1 to give the same results as obtained in Example 1. It has now been proved that the element of Example 1 as assembled into a solid state imaging device has low dark current even after heating, i.e., exhibits high heat resistance.

Industrial Applicability

The invention provides a photoelectric element containing a compound with specific characteristics and an imaging device having the photoelectric element. The photoelectric element has a low dark current and, when heated, undergoes no significant reduction in conversion efficiency.

This application is based on Japanese patent applications No. 2010-026993 filed on Feb. 9, 2010 and No. 2011-015843 filed on Jan. 27, 2011, the entire contents of which are hereby incorporated by reference, the same as if set forth at length.

The invention claimed is:

1. A photoelectric element comprising a conductive layer, an organic photoelectric layer, a blocking layer and a transparent conductive layer,
    the organic photoelectric layer comprising a p type organic photoelectric material having a glass transition temperature of 100° C. or higher and forming an amorphous layer, and
    the blocking layer comprising a blocking material having a glass transition temperature of 140° C. or higher.

2. The photoelectric element according to claim 1, wherein the blocking layer is an electron blocking layer.

3. The photoelectric element according to claim 2, wherein the blocking material is a triarylamine.

4. The photoelectric element according to claim 3, wherein the triarylamine is represented by the following formula (V):

Formula (V):

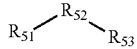

wherein $R_{51}$, $R_{52}$ and $R_{53}$ each independently represent a group containing an aryl group or a group containing a heteroaryl group, provided that at least one of $R_{51}$, $R_{52}$, and $R_{53}$ contains one nitrogen atom.

5. The photoelectric element according to claim 2 wherein the blocking material has an ionization potential of 4.7 to 5.8 eV.

6. The photoelectric element according to claim 1 wherein the blocking material has an absorption maximum at a wavelength of 400 nm or shorter.

7. The photoelectric element according to claim 1, wherein the p type organic photoelectric material is a p type organic semiconductor, and the organic photoelectric layer is a mixture of the p type organic semiconductor and an n type organic semiconductor.

8. The photoelectric element according to claim 1, wherein the p type organic photoelectric material has an absorption maximum in the wavelength range of from 450 nm to 620 nm and a molar extinction coefficient of 30,000 $M^{-1}cm^{-1}$ or more at the absorption maximum wavelength.

9. The photoelectric element according to claim 1, wherein the p type organic photoelectric material has an ionization potential of 4.5 to 5.8 eV.

10. The photoelectric element according to claim 1, wherein the p type organic photoelectric material is represented by the following formula (I):

Formula (I):

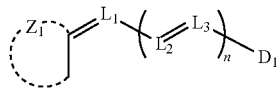

wherein $Z_1$ represents a ring structure containing at least two carbon atoms selected from a 5-membered ring, a 6-membered ring, and a fused ring structure having at least one of a 5-membered ring and a 6-membered ring; $L_1$, $L_2$, and $L_3$ each independently represent a methine group or a substituted methine group; $D_1$ represents an aryl group or a heteroaryl group; and n represents an integer of 0 or greater.

11. An imaging device comprising the photoelectric element according to claim 1.

12. A method for driving the photoelectric element according to claim 1, comprising applying an electric field of $1\times10^{-4}$ V/cm to $1\times10^7$ V/cm between the conductive layer and the transparent conductive layer serving as a pair of electrodes.

13. The method according to claim 12, wherein the electron blocking layer is in contact with one of the electrodes, and the electric field is applied, with the electrode with which the electron blocking layer is in contact as a negative electrode and the opposing electrode as a positive electrode.

14. The method according to claim 12, wherein light is allowed to impinge on the side of the electrode not being in contact with the electron blocking layer.

* * * * *